US011224722B2

(12) United States Patent
Moreno et al.

(10) Patent No.: US 11,224,722 B2
(45) Date of Patent: Jan. 18, 2022

(54) DEVICES, SYSTEMS AND METHODS FOR TRACKING TRAVEL OF AN ELONGATED MEDICAL DEVICE

(71) Applicant: Xact Anesthesia, LLC, Huntley, IL (US)

(72) Inventors: Carlos Xavier Moreno, Huntley, IL (US); James P. Orrico, Evanston, IL (US)

(73) Assignee: Xact Anesthesia, LLC, Huntley, IL (US)

( * ) Notice: Subject to any disclaimer, the term of this patent is extended or adjusted under 35 U.S.C. 154(b) by 182 days.

(21) Appl. No.: 16/403,792

(22) Filed: May 6, 2019

(65) Prior Publication Data

US 2020/0353213 A1    Nov. 12, 2020

(51) Int. Cl.
| | | |
|---|---|---|
| *A61M 25/01* | (2006.01) | |
| *A61B 90/00* | (2016.01) | |
| *A61M 25/09* | (2006.01) | |
| *A61M 25/00* | (2006.01) | |

(52) U.S. Cl.
CPC .. *A61M 25/0113* (2013.01); *A61M 25/09041* (2013.01); *A61B 2090/0807* (2016.02); *A61M 2025/0007* (2013.01)

(58) Field of Classification Search
CPC ........ A61M 25/0113; A61M 25/09041; A61M 2025/0007; A61M 2025/0008; A61B 2090/0807; A61B 1/00066
See application file for complete search history.

(56) References Cited

U.S. PATENT DOCUMENTS

| | | | | |
|---|---|---|---|---|
| 4,397,091 A | * | 8/1983 | Gustavsson | ........ A61M 25/0113 33/732 |
| 5,297,346 A | * | 3/1994 | Weiner | ................. A61B 5/1076 33/512 |
| 5,318,541 A | * | 6/1994 | Viera | .............. A61M 25/09041 604/159 |
| 5,611,778 A | * | 3/1997 | Brinon | .................. A61M 25/01 604/117 |

(Continued)

OTHER PUBLICATIONS

Singh S, Sagadai S. "Epidural catheter markings and the morbidly obese". International Journal of Obstetric Anesthesia, Jul. 2010, p. 350-351.

*Primary Examiner* — Bhisma Mehta
*Assistant Examiner* — John J Crawford
(74) *Attorney, Agent, or Firm* — Dicke, Billig & Czaja, PLLC

(57) ABSTRACT

A counter device for use in tracking an elongated medical device. The counter device includes a housing assembly and a tracking and display unit. The housing assembly defines an entrance opening, an exit opening, and a passageway. The passageway is open to and extends between the entrance and exit openings. The tracking and display unit is carried by the housing assembly and is configured to selectively interface with an elongated medical device disposed along the passageway. In a tracking state, the tracking and display unit generates information indicative of a distance of travel of the elongated medical device traveling along the passageway. In some embodiments, the tracking and display unit includes an engagement assembly rotatably coupled to the housing assembly. The engagement assembly can have a toothed engagement face.

19 Claims, 17 Drawing Sheets

(56) References Cited

U.S. PATENT DOCUMENTS

| | | | |
|---|---|---|---|
| 5,725,504 A | 3/1998 | Collins | |
| 6,042,562 A * | 3/2000 | Amor | A61M 25/00 |
| | | | 116/284 |
| 6,494,848 B1 | 12/2002 | Sommercorn et al. | |
| D489,452 S | 5/2004 | Schweikert | |
| 2003/0094731 A1 | 5/2003 | Simpson | |
| 2007/0083184 A1* | 4/2007 | Simpson | A61M 25/0113 |
| | | | 604/500 |
| 2007/0250006 A1* | 10/2007 | Court | A61B 90/06 |
| | | | 604/117 |
| 2010/0130923 A1* | 5/2010 | Cleary | A61M 25/0113 |
| | | | 604/95.04 |
| 2010/0174290 A1* | 7/2010 | Wuebbeling | A61F 2/95 |
| | | | 606/108 |

* cited by examiner

DEVICES, SYSTEMS AND METHODS FOR TRACKING TRAVEL OF AN ELONGATED MEDICAL DEVICE

BACKGROUND

The present disclosure is directed to devices for facilitating performance of a medical procedure. More particularly, it relates to devices for tracking a travel distance of an elongated medical device during insertion thereof into a patient, such as an epidural catheter as part of an epidural anesthesia administration procedure.

Many medical procedures involve the insertion of an elongated medical device through the patient's skin. In most instances, the clinician benefits from knowing a location of a distal end of the so-inserted medical device relative to the patient's anatomy. While imaging or other related technology is utilized with certain procedures to visualize features of an inserted device, such equipment can be highly expensive, can significantly increase the overall procedure time, and requires a trained specialist to operate. As such, clinicians are oftentimes asked to rely on their experience to estimate a location of a medical device inserted through the skin.

For example, epidural anesthesia procedures are performed to administer or inject a local anesthetic agent (and perhaps other substances) into the epidural space around the spinal cord. The epidural anesthesia procedure normally includes the insertion of a spinal needle (e.g., a Tuohy needle) at the patient's back, between targeted spinous processes (e.g., midline or paramedian approach), locating the needle tip at the epidural space. Various techniques can be employed to confirm that the needle tip is satisfactorily positioned. An epidural catheter is then advanced through the needle and into the patient until a length of the catheter extends beyond the needle tip and into the epidural space. The needle is then withdrawn over the catheter. Anesthetics are then injected into the epidural space via the catheter. The clinician cannot see the distal end of the catheter as it is being advanced beyond the needle tip, and it can be important to ensure that the distal end has achieved, but not progressed beyond, a desired location/distance from the needle tip. Some epidural catheters have graduated markings along their exterior; by visually monitoring the markings that are otherwise visible proximal the needle, the clinician can attempt to deduce or calculate a distance the catheter has been advanced. This can be a difficult task and may not be reliable. More often, the clinician is left to grossly estimate the length of catheter that is in the epidural space by feel and experience.

Other medical procedures involving the blind insertion of the distal end of an elongated medical device into a patient's body raise similar concerns. For example, absent visualization equipment, it can be difficult at best for a clinician to gauge the extent to which a guidewire has been advanced.

SUMMARY

The inventor of the present disclosure has recognized a need to address one or more of the above-mentioned problems.

Some aspects of the present disclosure are directed to a counter device for use with an elongated medical device. The counter device includes a housing assembly and a tracking and display unit. The housing assembly defines an entrance opening, an exit opening, and a passageway. The passageway is open to and extends between the entrance and exit openings. The tracking and display unit is carried by the housing assembly and is configured to selectively interface with an elongated medical device disposed along the passageway. The counter device is configured to provide a tracking state in which the tracking and display unit generates information indicative of a distance of travel of an elongated medical device traveling along the passageway. In some embodiments, the tracking and display unit includes an engagement assembly that is configured to selectively engage an elongated medical device disposed along the passageway and that is rotatably coupled to the housing assembly. In related embodiments, the engagement assembly provides a toothed engagement face. In some embodiments, the tracking and display unit includes indicia disposed on an engagement assembly and a window formed in the housing assembly; portions of the indicia are selectively visible in the window to convey a distance of travel value. In some embodiments, the counter device further includes an actuator assembly configured to selectively bring an elongated medical device disposes along the passageway into engagement with the tracking and display unit.

Other aspects of the present disclosure are directed to a kit for performing a medical procedure. The kit include an elongated medical device and a counter device. The counter device includes a housing assembly and a tracking and display unit. The housing assembly defines an entrance opening, an exit opening, and a passageway. The passageway is open to and extends between the entrance and exit openings. The tracking and display unit is carried by the housing assembly and is configured to selectively interface with an elongated medical device disposed along the passageway. The counter device is configured to slidably receive the elongated medical device along the passageway. The counter device is further configured to provide a tracking state in which the tracking and display unit generates information indicative of a distance of travel of the elongated medical device traveling along the passageway. In some embodiments, the elongated medical device is an epidural catheter and the kit further includes packaging sealed about the counter device and the epidural catheter.

Yet other aspects of the present disclosure are directed to a method of performing a medical procedure on a patient. The method includes receiving a counter device. The counter device comprises a housing assembly and a tracking and display unit. The housing assembly defines an entrance opening, an exit opening, and a passageway. The passageway is open to and extends between the entrance and exit openings. The tracking and display unit is carried by the housing assembly. An elongated medical device is inserted into the passageway such that a first portion of the elongated medical device extends proximally from the entrance opening and a second portion extends distally from the exit opening. The counter device is transitioned to a tracking state. The elongated medical device is distally advanced relative to the counter device and into the patient. During the step of distally advancing, the tracking and display unit generates and displays information indicative of a distance of travel of the elongated medical device into the patient. In some embodiments, the elongated medical device is an epidural catheter, and the method further includes delivering a liquid into the patient via the epidural catheter.

DETAILED DESCRIPTION

Figure 1A:
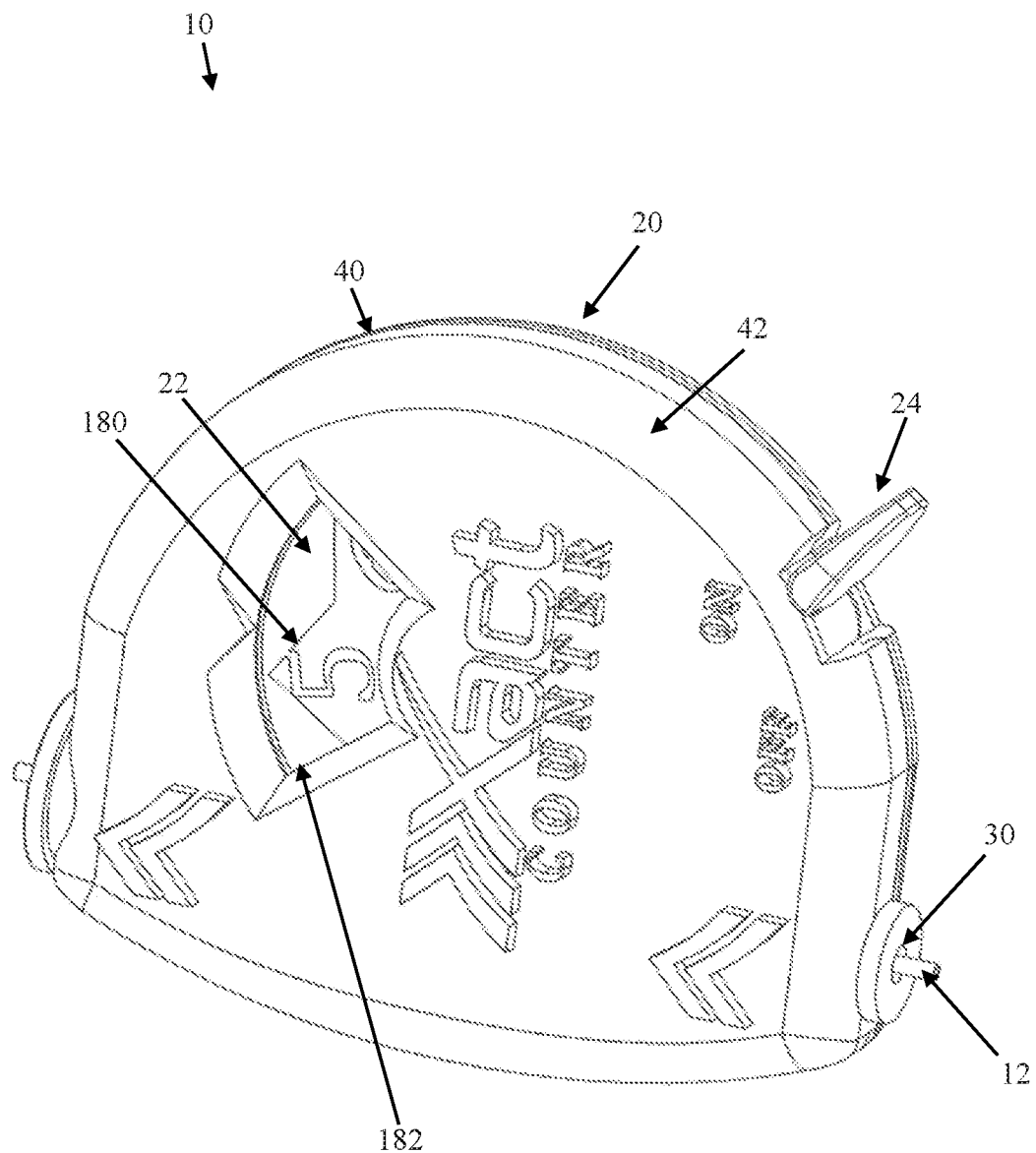
FIG. 1A is a perspective view of a counter device in accordance with principles of the present disclosure and interfacing with an elongated medical device.
Figure 1B:
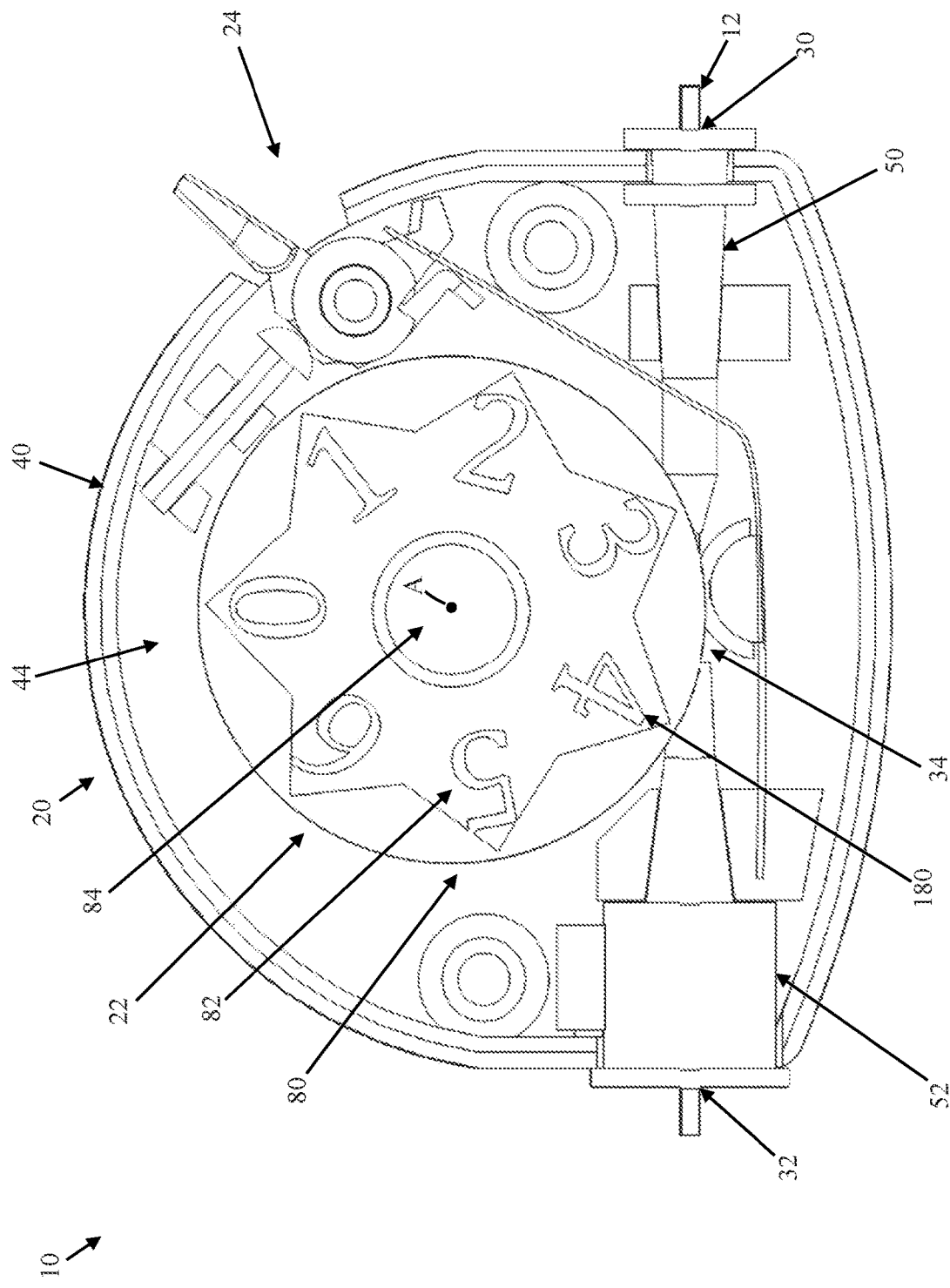
FIG. 1B is an enlarged top plan view of the counter device of FIG. 1A with a portion of a cover assembly removed.

Some aspects of the present disclosure are directed to devices, systems and methods for tracking (or "counting") advancement of an elongated medical device into a patient as part of a medical procedure, for example advancement of an epidural catheter as part of an epidural anesthesia administration procedure. One embodiment of a counter device 10 in accordance with principles of the present disclosure is shown in FIGS. 1A and 1B, interfacing with an elongated medical device 12. As described below, the counter device 10 is operable to indicate a distance or length of the travel of the elongated medical device 12 relative to the counter device 10 (and optionally vice-versa). In this regard, the counter device 10 is useful with various different elongated medical devices 12 including, but not limited to, a catheter (e.g., an epidural catheter), a guidewire, etc.

The counter device 10 generally includes a housing assembly 20, a tracking and display unit 22 (referenced generally), and an optional actuator assembly 24. Details on the various components are provided below. In general terms, the housing assembly 20 defines an entrance opening 30, an exit opening 32, and a passageway 34 (referenced generally in FIG. 1B) open to and extending between the entrance and exit openings 30, 32. In the view of FIG. 1B, the passageway 34 is occupied by the elongated medical device 12. The tracking and display unit 22 is carried by the housing assembly 20 and is configured to selectively interface with the elongated medical device 12 disposed along the passageway 34. In this regard, the counter device 10 is configured to provide a tracking or engaged state in which the tracking and display unit 22 generates information indicative of a distance of travel of the elongated medical device 12 traveling along the passageway 34. The so-generated information can be conveyed to a user as described below, for example as depicted in FIG. 1A. Where provided, the actuator assembly 24 is operable to transition the counter device 10 between the tracking state and a free state in which the tracking and display unit 22 does not actively track the elongated medical device 12 otherwise traveling along the passageway 34. As a point of reference, the counter device 10 is shown in an "on" or "tracking" state in the views of FIGS. 1A and 1B.

Housing Assembly

The housing assembly 20 can assume various forms, and in some embodiments includes an outer housing 40 formed, for example, by front and rear housing sections 42, 44 that combine to define an open interior volume. The front housing section 42 is shown in FIG. 1A, and is removed in the view of FIG. 1B so as make visible various components maintained within the open interior volume. The housing sections 42, 44 can be separated formed and subsequently assembled to one another in various fashions. In other embodiments, the outer housing 40 can be generated by three or more housing sections; in yet other embodiments, the outer housing 40 can be a single, integral or homogenous body.

Figure 2A:
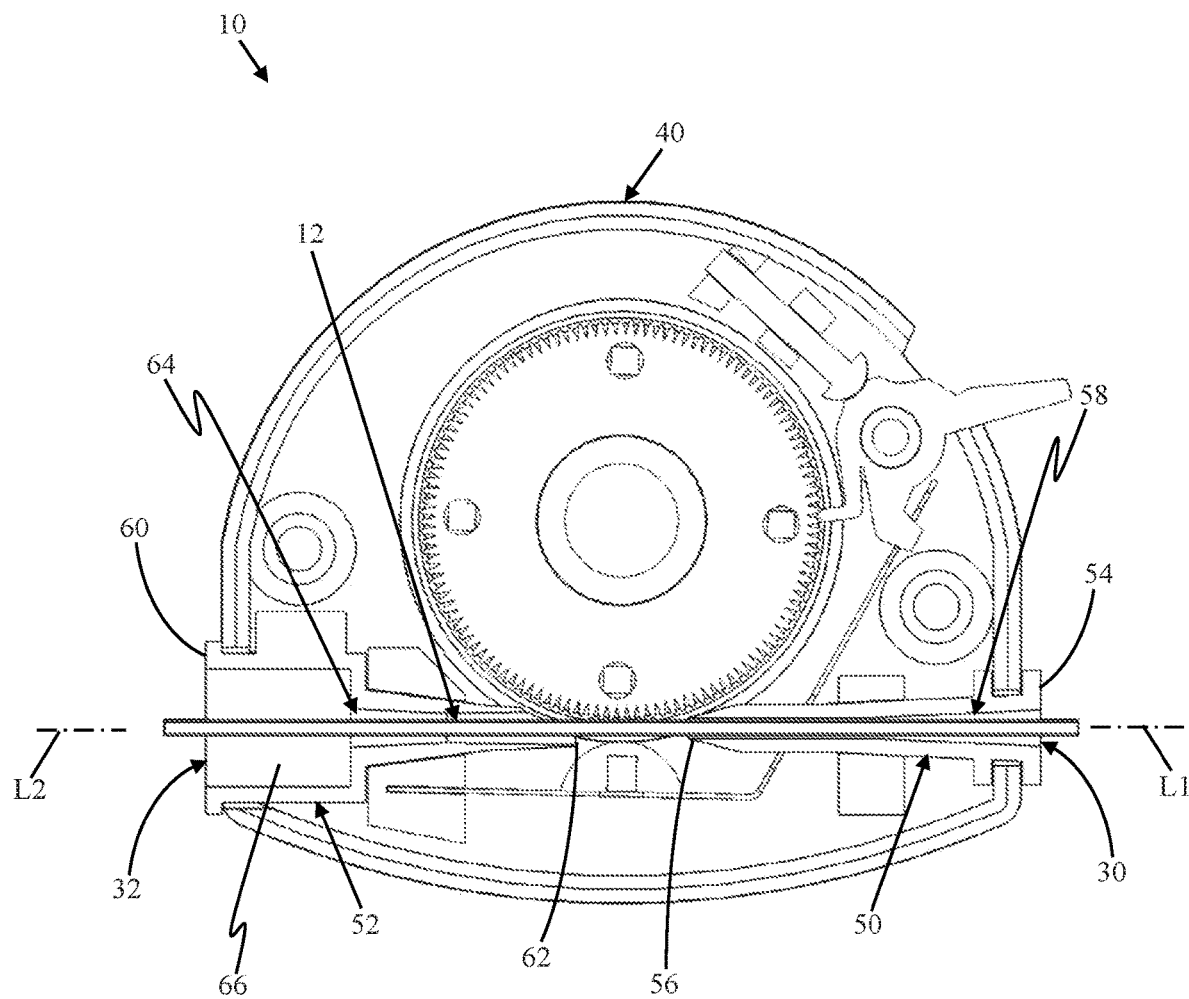
FIG. 2A is a lateral cross-sectional view of the counter device of FIG. 1A and in an off or no tracking state.

The housing assembly 20 can establish the entrance opening 30, the exit opening 32, and the passageway 34 in a variety of manners. In one non-limiting embodiment, for example, the housing assembly 20 includes an entrance funnel 50 and an exit funnel 52. With additional reference to FIG. 2A, the entrance funnel 50 extends between opposing, first and second ends 54, 56, and defines an entrance passage or lumen 58. As a point of reference, in the view of FIG. 2A, the counter device 10 is shown in an "off" or no tracking state (as compared to the "on" or tracking state of FIGS. 1A and 1B) for ease of understanding. The entrance funnel 50 is assembled to and maintained by the outer housing 40 such that the first end 54 projects beyond the outer housing 40. The entrance passage 58 is open at the first end 54 and thus serves as the entrance opening 30. A diameter of the entrance passage 58 can taper from the first end 54 in a direction of the second end 56, with a minimum diameter of the entrance passage 58 (i.e., at least in a region of the second end 56) approximating an expected diameter of the elongated medical device 12 to be utilized with the counter device 10. Regardless, the entrance passage 58 defines a longitudinal axis L1, and the entrance funnel 50 is assembled to the outer housing 40 so as to minimize possible overt movement of the entrance funnel 50 relative to the outer housing 40 (e.g., the entrance funnel 50 is mounted to the outer housing 40 such that the entrance funnel 50 cannot move or deflect in a direction perpendicular to the longitudinal axis L1).

The exit funnel 52 extends between opposing, first and second ends 60, 62, and defines an exit passage or lumen 64. The exit funnel 62 is assembled to and maintained by the outer housing 50 such that the first end 60 projects beyond the outer housing 40. The exit passage 64 is open at the first end 60 and thus serves as the exit opening 32. A diameter of the exit passage 64 can generally taper in a direction of the second end 62. In some non-limiting embodiments, a diameter of the exit passage 64 can be enlarged in a port region 66 of the first end 60, formatted to receive an end or port of a separate or auxiliary medical device component, such as a spinal needle, luer lock, etc. In other embodiments, the port region 66 can be omitted. Regardless, the exit passage 64 defines a longitudinal axis L2, and the exit funnel 52 is assembled to the outer housing 40 so as to minimize possible overt movement of the exit funnel 52 relative to the outer housing 40 (e.g., the exit funnel 52 is mounted to the outer housing 40 such that the exit funnel 52 cannot move or deflect relative to the outer housing 40 in a direction perpendicular to the longitudinal axis L2).

Figure 2B:
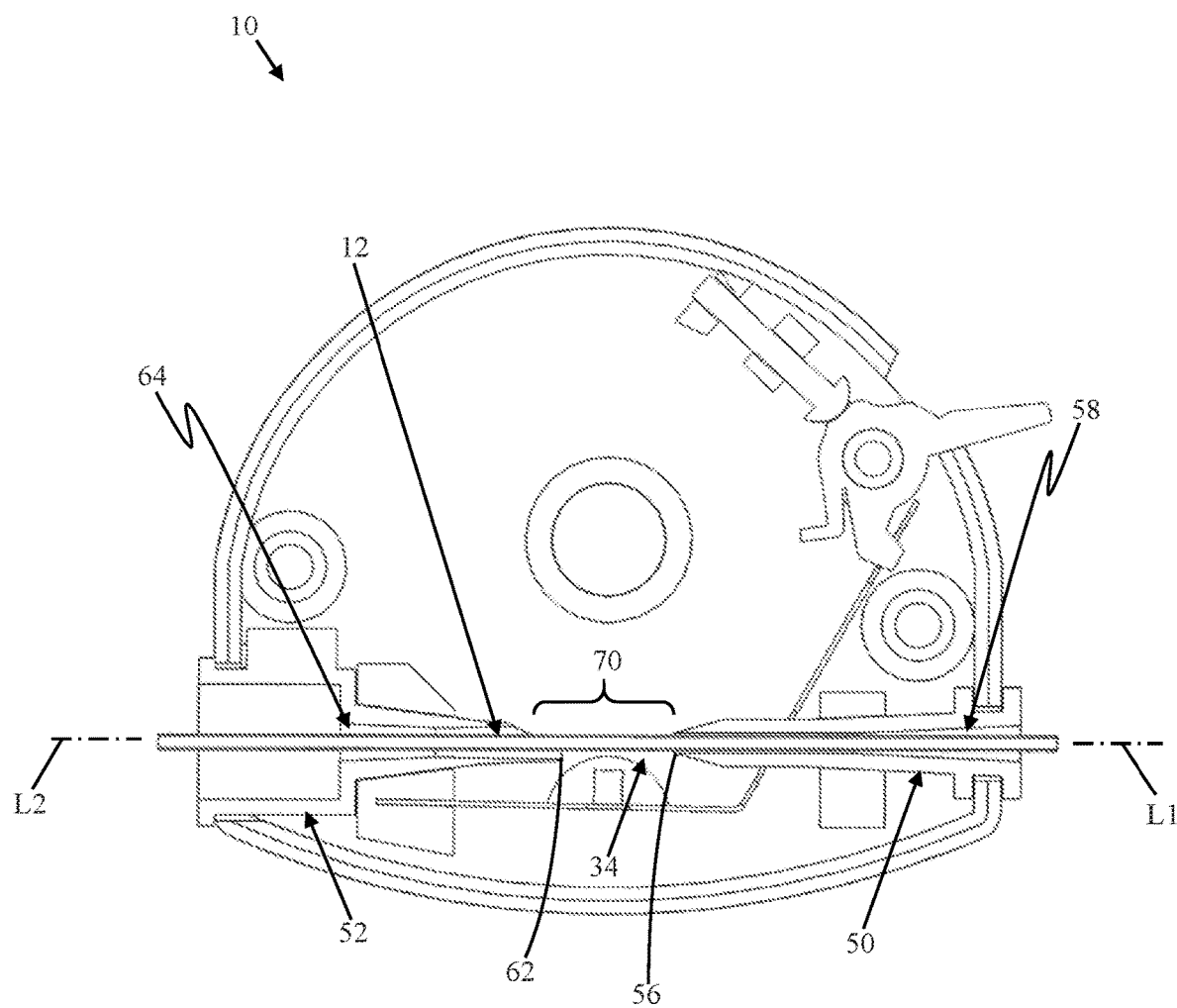
FIG. 2B is the lateral cross-sectional view of FIG. 2A with a portion of an engagement assembly removed.

In some embodiments, the passageway 34 can be established, at least in part, by a combination of the entrance passage 58 and the exit passage 64. For example, the entrance and exit funnels 50, 52 can be assembled to and maintained by the outer housing 40 such that the corresponding longitudinal axes L1, L2 are aligned. FIG. 2B is the cross-sectional view of FIG. 2A, but with portions of the tracking and display unit 22 removed. As shown, the second end 56 of the entrance funnel 50 is spaced from the second end 62 of the exit funnel 52, establishing a gap 70 for reasons made clear below. Due to the aligned arrangement of the entrance and exit passages 58, 64, the space or volume of the gap 70 can be considered "part" of the passageway 34; as shown, the elongated medical device 12 can be disposed through and along the passageway 34, extending through and from the entrance passage 58, across the gap 70, and to and through the exit passage 64. Moreover, the passageway 34 is configured to permit the elongated medical device 12 to travel along the passageway 34, and thus relative to the counter device 10. More particularly, the passageway 34 is configured such that the elongated medical device 12 is permitted to travel longitudinally through the passageway 34 (e.g., leftward or rightward relative to the orientation of FIG. 2B), in a direction generally parallel with the longitudinal axes L1, L2.

The entrance opening 30, the exit opening 32, and the passageway 34 can alternatively be formed or established in other manners not directly implicated by the views. For example, in some embodiments, one or both or the funnels 50, 52 can be omitted or replaced by a different component. Further, the housing assembly 20 can incorporate additional components that establish segments of the passageway 34 conducive to receiving and directing the elongated medical device 12 in a desired manner.

Tracking and Display Unit

Returning to FIG. 1B, the tracking and display unit 22 can assume various forms appropriate for selectively interfacing with the elongated medical device 12 as the elongated medical device 12 travels along the passageway 34. In some embodiments, the tracking and display unit 22 includes an engagement assembly 80 and a display assembly 82 (referenced generally). In general terms, the engagement assembly 80 is configured to engage the elongated medical device 12 traveling along the passageway 34 in a manner that tracks a distance of travel, and the display assembly 82 is configured to display information to a user indicative of the tracked distance of travel.

Figure 3A:
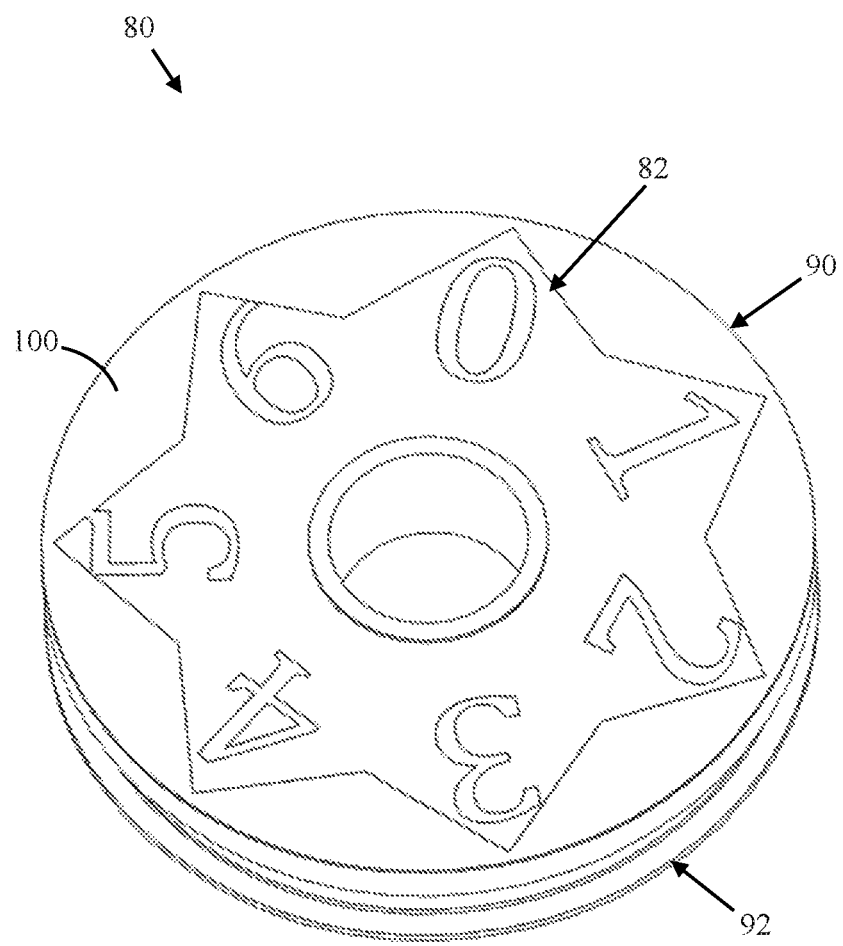
FIG. 3A is a perspective view of an engagement assembly useful with the counter device of FIG. 1A.
Figure 3B:
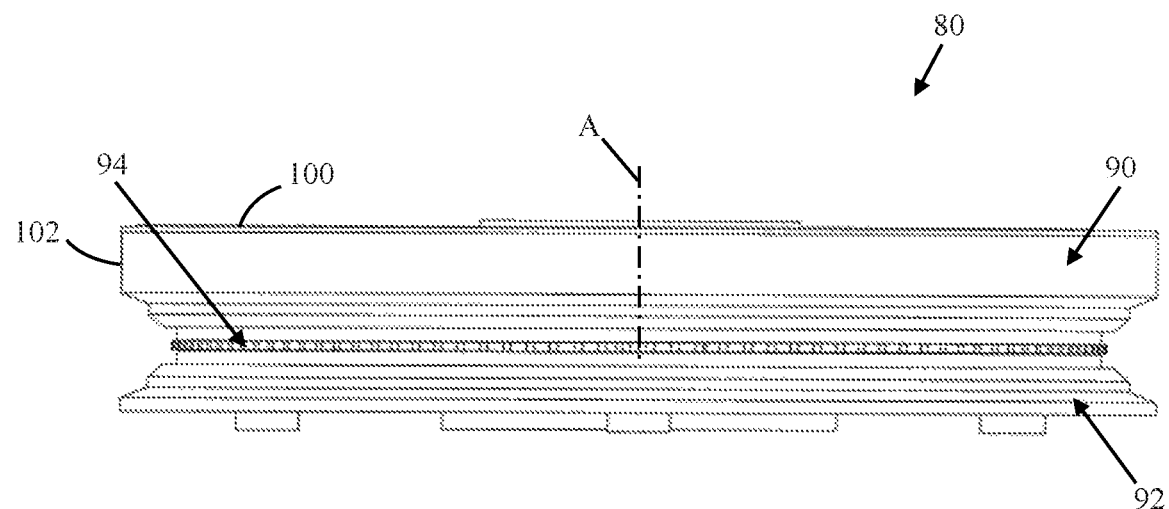
FIG. 3B is a side plan view of the engagement assembly of FIG. 3A.
Figure 3C:
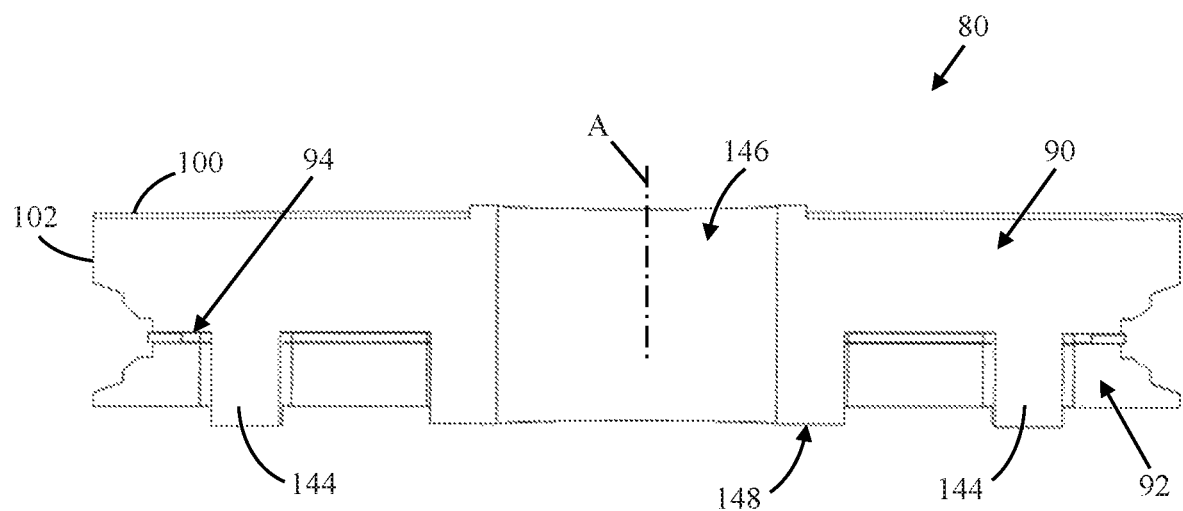
FIG. 3C is a longitudinal cross-sectional view of the engagement assembly of FIG. 3A.

The engagement assembly 80 can assume various forms, and in some embodiments, is configured to be rotatably coupled to the housing assembly 20, for example about a central axis A established by a pin 84. The engagement assembly 80 can have a wheel-like or spool-like shape, and can be comprised of two or more components or bodies. One embodiment of the engagement assembly 80 is shown in isolation in FIGS. 3A-3E (it being understood that a portion of one embodiment of the display 82 is also visible in FIG. 3A and is referenced generally). The engagement assembly 80 includes a first outer hub body 90, a second outer hub body 92, and a ring 94. The ring 94 is disposed, or sandwiched, between the hub bodies 90, 92. Upon final assembly, the engagement assembly 80 establishes, and is rotatable about, a central axis commensurate with the central axis A described above.

The first hub body 90 forms or defines an upper surface 100 and a side surface 102. The side surface 102 establishes an outer perimeter, diameter or radius of the first hub body 90, and projects longitudinally from the upper surface 100. With specific reference to FIG. 3D, a geometry of the first hub body 90 along the side surface 102 generates a flange region 104 and an interface region 106. The diameter of the first hub body 90 along the flange region 104 is greater than the diameter along the interface region 106 (e.g., a geometry of the side surface 102 can have a step-down configuration from the flange region 104 to and along the interface region 106). The interface region 106 includes or defines a guide face 108, a capture face 110 and support face 112. The diameter of the first hub body 90 can gradually taper or decrease along the guide face 108 in extension from the flange region 104 to the capture face 110 (e.g., relative to the cross-sectional view of the FIG. 3D, a plane of the guide face 108 can be non-parallel and non-perpendicular to the central axis A). Extension of the capture face 110 between the guide face 108 and the support face 112 can establish a plane that is substantially perpendicular (i.e., within 5 degrees of a truly perpendicular arrangement) to the central axis A. A diameter of the first hub body 90 along the support face 112 can be substantially uniform (i.e., within 5 percent of a truly uniform diameter surface).

The second hub body 92 can have a similar construction and forms or defines a lower surface 120 and a side surface 122. The side surface 122 establishes an outer perimeter, diameter or radius of the first hub body 92, and projects longitudinally from the lower surface 120. A geometry of the second hub body 92 along the side surface 122 generates a flange region 124 and an interface region 126. The diameter of the second hub body 92 along the flange region 124 is greater than the diameter along the interface region 126 (e.g., a geometry of the side surface 122 can have a step-down configuration from the flange region 124 to and along the interface region 126). The interface region 126 includes or defines a guide face 128, a capture face 130 and support face 132. The diameter of the second hub body 92 can gradually taper or decrease along the guide face 128 in extension from the flange region 124 to the capture face 130 (e.g., relative to the cross-sectional view of the FIG. 3D, a plane of the guide face 128 can be non-parallel and non-perpendicular to the central axis A). Extension of the capture face 130 between the guide face 128 and the support face 132 can establish a plane that is substantially perpendicular (i.e., within 5 degrees of a truly perpendicular arrangement) to the central axis A. A diameter of the second hub body 92 along the support face 132 can be substantially uniform (i.e., within 5 percent of a truly uniform diameter surface).

The ring 94 can assume various forms, and is generally configured to robustly engage (e.g., mechanically engage, frictionally engage, etc.) an elongated medical device, for example a conventional epidural catheter that typically exhibits a hard, but slick or lubricious surface. For example, the ring 94 defines an engagement face 140 at perimeter thereof. As best shown in FIG. 3E, in some embodiments, the engagement face 140 can be formed or defined by a plurality of teeth 142 (e.g., the engagement face 140 is a toothed surface). Other constructions are also acceptable (e.g., the engagement face 140 can be a knurled surface, etc.). In related embodiments, the ring 94 can be formed of a hardened material selected to have an enhanced coefficient of friction with selected materials (e.g., with the lubricious, polymer surface of many epidural catheters). For example, in some embodiments the ring 94 is formed of metal that is photo-etched to generate the teeth 142. Other materials are also acceptable. In yet other embodiments, the ring 94 can be omitted, for example where the elongated medical device 12 (FIG. 1A) to be tracked exhibits material characteristics conducive to frictional engagement with a relatively smooth surface.

The hub bodies 90, 92 and the ring 94 can incorporate various features that promote construction of the engagement assembly 80. For example, and as generally reflected by FIG. 3C, the first hub body 90 can form or define one or more posts 144, with the second hub body 92 and the ring 94 defining channel(s) in which a corresponding one of the posts 144 is received. The post(s) 144 can then be affixed to the second hub body 92 (e.g., welded). Other mounting features or techniques are equally acceptable. Regardless, the engagement assembly 80 provides a central aperture 146 (e.g., optionally defined by the first hub body 90) sized to rotatably receive the pin 84 (FIG. 1B), and a bearing surface 148 (optionally defined by the first hub body 90). In other embodiments, the aperture 146 can be omitted (e.g., by integrating the pin 84 with the engagement assembly 80).

Figure 3D:
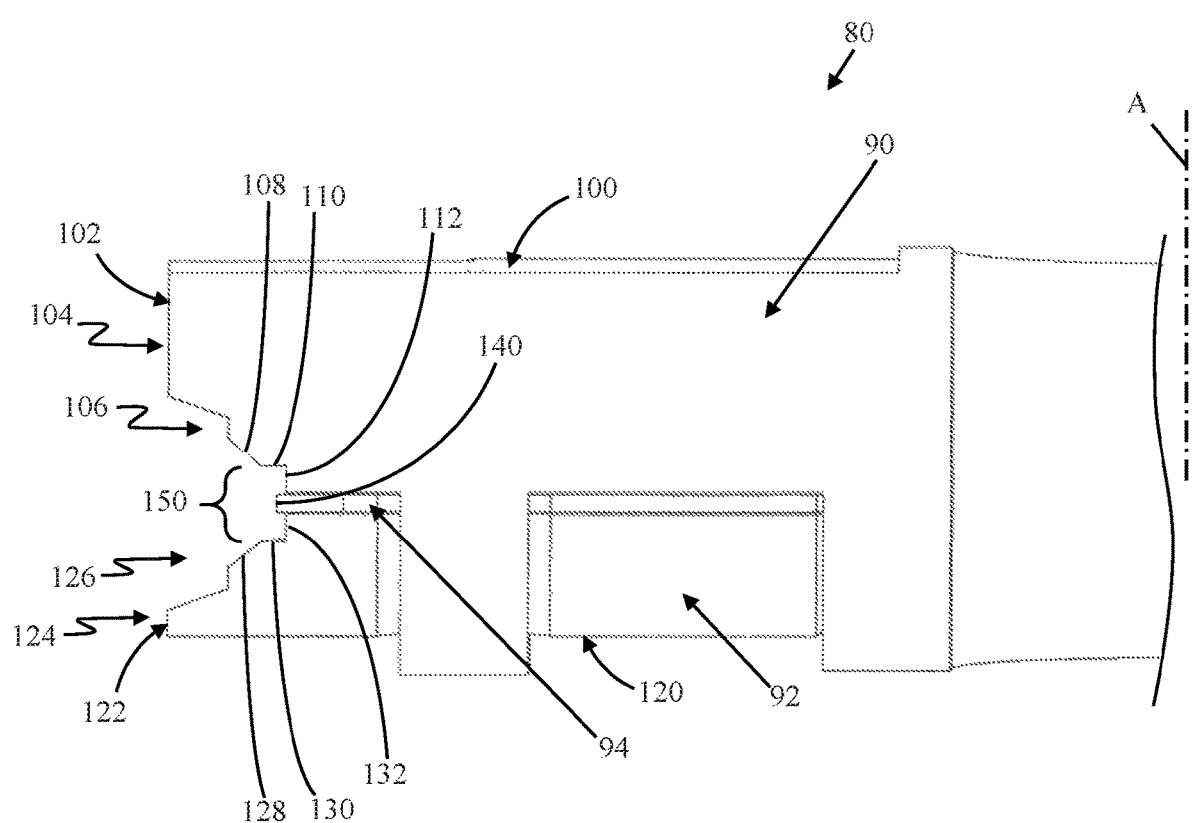
FIG. 3D is an enlarged portion of the cross-sectional view of FIG. 3C.
Figure 3E:
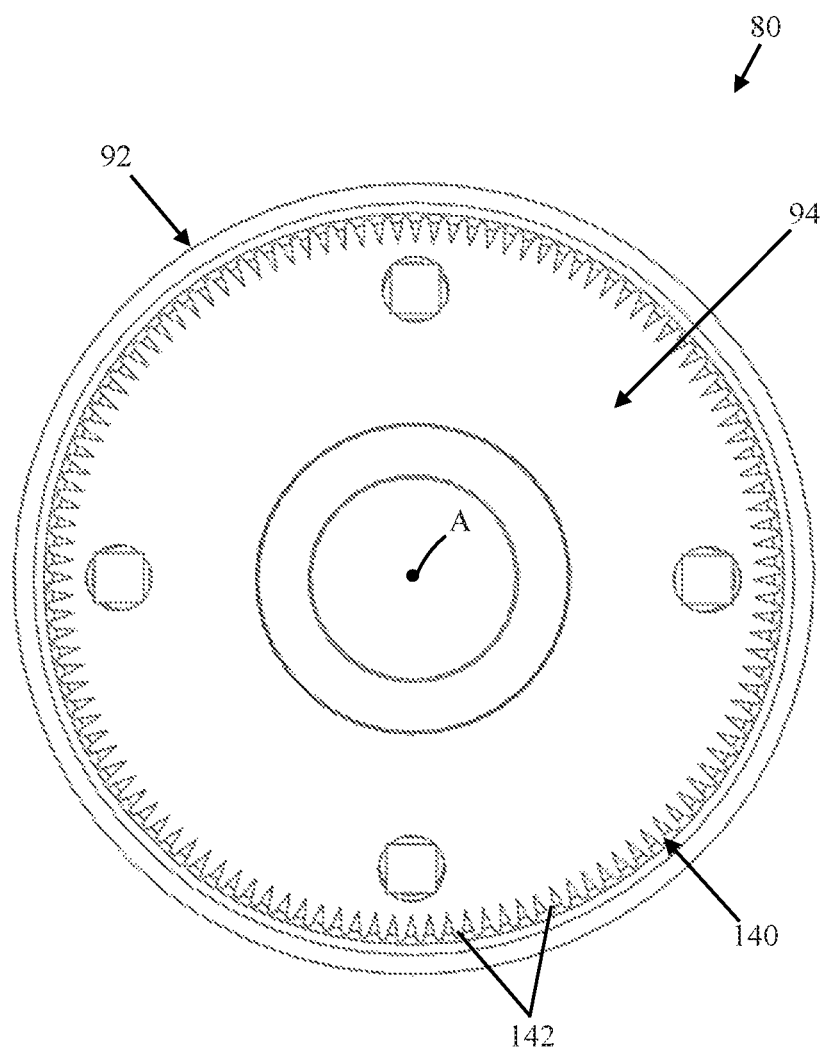
FIG. 3E is a lateral cross-sectional view of the engagement assembly of FIG. 3A.

With reference to FIG. 3D, upon final assembly, the engagement assembly 80 establishes a capture zone 150 between the capture face 110 of the first hub body 90 and the capture face 130 of the second hub body 92. A geometry of the ring 94 can be selected to establish an outer diameter that is greater than the outer diameter of the hub bodies 90, 92 along the corresponding support faces 112, 132. Thus, within the capture zone 150, the ring 94 projects radially or transversely (relative to the central axis A) beyond the support face 112 of the first hub body 90 and the support face 132 of the second hub body 92. With this construction, as an elongated medical device (not shown) is directed radially (relative to the central axis A) into the capture zone 150 (or vice-versa), the elongated medical device will contact, or be engaged by, the engagement face 140 of the ring 94. The tapered geometry of the guide faces 108, 128 assist in guiding the elongated medical device toward the engagement face 140, and the capture faces 110, 130 prevent the elongated medical device from overtly moving longitudinally relative to the engagement face 140. Because expected engaged interface with the elongated medical device is primarily at the ring 94, the hub bodies 90, 92 need not be formed of a material having a higher coefficient of friction with the expected elongated medical device. Thus, for example, where the ring 94 is metal, the hub bodies 90, 92 can be formed or molded of a polymer material or resin, and the various faces of the hub bodies 90, 92 can be relatively smooth. Other materials, such as metal, can alternatively be employed for one or both of the hub bodies 90, 92. In yet other embodiments, the engagement assembly 80 can be formed by more or less than three components; regardless, the engagement assembly 80 establishes or provide the engagement face 140 at which robust contact with an elongated medical device being tracked by the counter device 10 (FIG. 1A) occurs.

An outer diameter, and thus a circumference, of the engagement face 140, can be selected to have a pre-determined correlation with expected travel distances and units of measure of interest to a user of the counter device 10 for reasons made clear below. For example, the circumference of the engagement face 140 can be substantially equal to a whole number of a selected units of measurement (i.e., within 5 percent of a whole number of a selected units of measurement). In some embodiments, the units of measurement of interest is centimeters, and the circumference of the engagement face 140 is substantially equal to a whole number of centimeters. Other units of measurement are also acceptable. In some embodiments, an expected travel distance of interest is less than 10 centimeters, optionally less than 8 centimeters, and the corresponding circumference of the engagement face 140 is less than 10 centimeters, optionally less than 8 centimeters. In some non-limiting embodiments, the circumference of the engagement face is substantially equal to 7 centimeters. These and other embodiments can be useful under circumstances in which the counter device 10 (FIG. 1A) is used to track an epidural catheter as part of an epidural anesthesia administration procedure (in which the expected travel distance of interest of the epidural catheter during the tracking operation is not expected to exceed 7 centimeters). In yet other embodiments, the counter devices of the present disclosure can provide a virtually "unlimited" counting ability (e.g., the rotary encoder embodiments described below). Further, the counter devices of the present disclosure can provide movement tracking information to an end user of greater than 10 centimeters. For example, in some embodiments the counter devices of the present disclosure are useful with vascular access procedures (e.g., peripherally inserted central catheter, various central venous access lines, midline, etc.) and other medical procedures in which the counter device tracks and displays travel distances of an elongated medical device on the order of 60 centimeters or more.

Returning to FIGS. 1A and 1B, the display assembly 82 can assume various forms, and in some embodiments includes indicia 180 and a window 182. In general terms, the indicia 180 provides information indicative of incremental units of measurement, with select portions of the indicia 180 being visible to a user via the window 182. As described in greater detail below, the indicia 180 is formatted to correlate with a circumference of the engagement face 140 (FIG. 3D) and movement of the engagement assembly 80, and is located relative to the window 182 such that the portion of the indicia 180 visible in the window 182 is indicative of a particular travel distance as tracked by the engagement assembly 80.

Figure 4A:
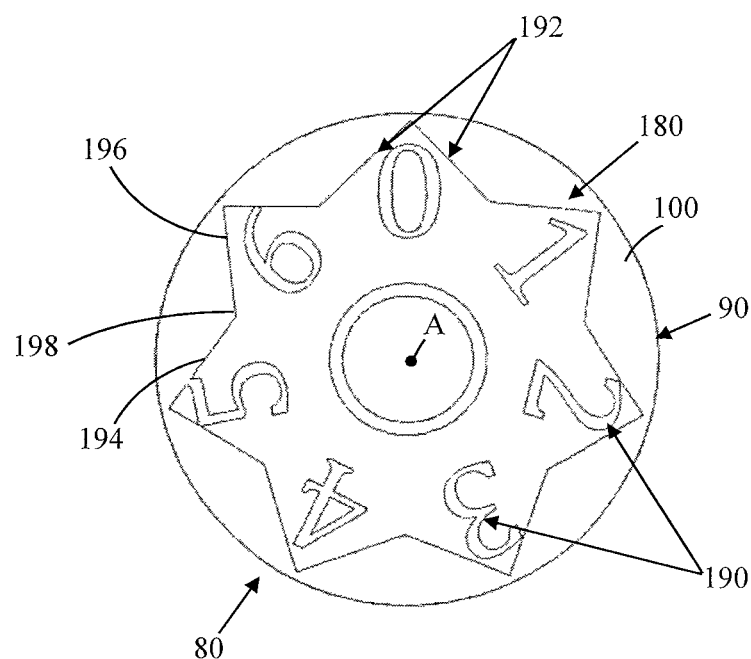
FIG. 4A is a top plan view of a portion of a display assembly useful with the counter device of FIG. 1A.

With reference to FIG. 4A, the indicia 180 can have any format useful in conveying travel distance information to a user, and in some embodiments includes a plurality of numbers or other numerical-type characters or symbols 190. The numbers 190 can be whole numbers, and can be equidistantly-spaced from one another relative to a circumference of the engagement face 140 (FIG. 3D) sequentially increasing in value in one rotational direction. In some embodiments, the numbers 190 are whole numbers and generally correspond (in value and location) with the selected units of measurement and circumference of the engagement face 140. For example, in the one non-limiting embodiment illustrated in FIG. 4A, the engagement face 140 has a circumference substantially equal to 7 centimeters, and the numbers 190 include the number "0", sequentially followed (in the clockwise direction relative to the orientation of FIG. 4A) by the numbers "1", "2", "3", "4", "5" and "6". Because the numbers 190 are equidistantly-spaced from one another, the circumferential distance between consecutive ones of the numbers 190 is substantially equal to 1 centimeter. Other formats or relationships of the numbers 190 are also envisioned (e.g., to correlate with a different diameter engagement face 140, a different unit of measurement (e.g., inches), etc.).

With embodiments in which the numbers 190 are whole numbers (and other embodiments), the indicia 180 can optionally further include increment indicators 192. The increment indicators 192 can assume various forms, and generally visually conveys information implicating an approximate circumferential distance between consecutive ones of the numbers 190. By way of non-limiting example, where the numbers 190 include the number "1" (implicating a distance of 1 centimeter) followed by the number "2" (implicating a distance of 2 centimeters), the increment indicators 192 can visually convey, for example, an approximate half-way point between "1" and "2" (implicating a distance of 1.5 centimeters). In some embodiments, the incremental indicators 192 can be an arrangement or pattern of lines, shapes and/or symbols (e.g., need not include a number character). For example, the incremental indicators 192 can include a pair of lines extending between a consecutive pair of the numbers 190 and that intersect at a point approximately one-half of the circumferential distance between the two consecutive numbers 190. By way of reference, a first line 194 and a second line 196 of the increment indicators 192 are identified in FIG. 4A. The first line 194 extends from a point approximately radially aligned (relative to the central axis A) with the number "5" in a direction generally toward the number "6"; the second line 196 extends from a point approximately radially aligned with the number "6" in a direction generally toward the number "5". The first and second lines 194, 196 intersect at a half-way point 198 that is otherwise circumferentially equidistantly-spaced between the numbers "5" and "6". A radial distance from the central axis A to the half-way point 198 is less than the radial distance from the central axis A to the initiation point of each of the lines 194, 196, thus giving the visual appearance of a taper or angle to each of the lines 194, 196 relative to the numbers "5" and "6". This visual appearance, in turn, readily conveys to a user an approximate incremental distance between the numbers "5" and "6" as described in greater detail below. The incremental indicators 192 can have other formats that may or may not include the lines 194, 196. In yet other embodiments, the incremental indicators 192 can be omitted.

Regardless of an exact configuration, the indicia 180 can be associated with the engagement assembly 80 in various manners. In some embodiments, the indicia 180 can be provided as a printed label affixed to the upper surface 100 of the first hub body 90. Alternatively, the indicia 180 can be printed, etched, molded etc., directly onto or into the upper surface 100. In other embodiments, the indicia 180 can be associated with one or more other components of the engagement assembly 80.

Figure 4B:
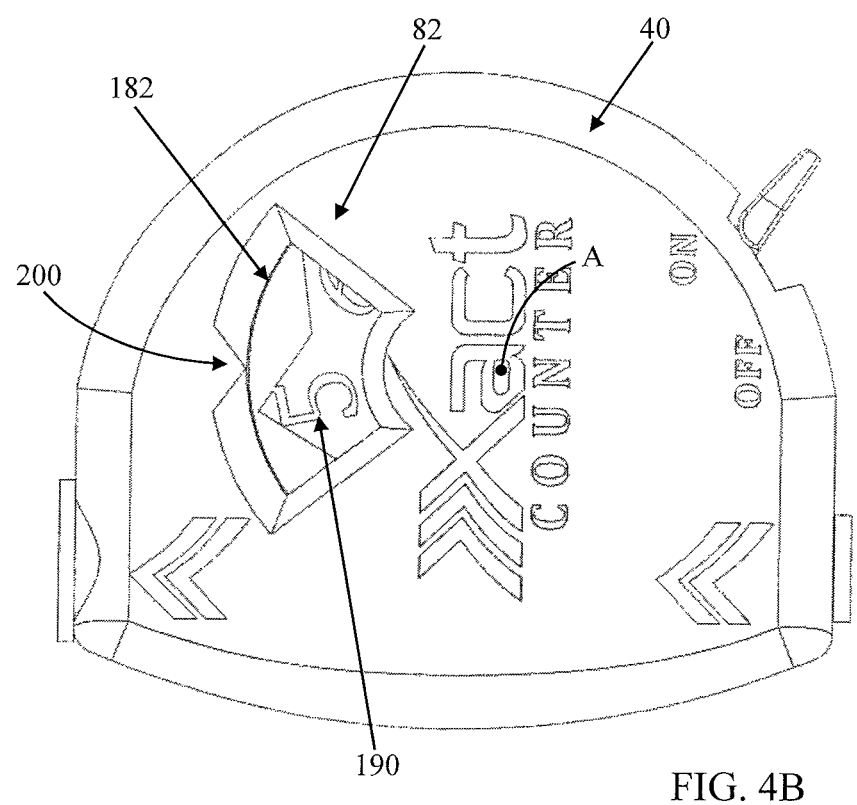
FIG. 4B is a top plan view of the counter device of FIG. 1A and illustrating an arrangement of the display assembly including the portion of FIG. 4A.

With reference to FIG. 4B, the window 182 can be defined through a thickness of the outer housing 40 at a radial distance from the central axis A corresponding with the indicia 180. A size and shape of the window 182 corresponds with a size of the numbers 190 (e.g., the window 182 is large enough so that individual ones of the numbers 190 are visible through the window 182). In some embodiments, the display assembly 82 can further include a pointer 200 or similar indicia on the front housing section 42 that visually conveys identification of a more precise point along the indicia 180. By way of reference, in the arrangement of FIG. 4B, the pointer 200 implicates a position along the indicia 180 in close proximity, but slightly greater than the number "5"; in some embodiments, this one example display can be perceived by a user as implicating a distance of approximately 5.1 centimeters (the pointer 200 is not directly aligned with the number "5", and instead is aligned with a location along the first line 194 (identified in FIG. 4A) that is closer to the number "5" than the half-way point 198 (identified in FIG. 4A)). In other embodiments, the pointer 200 or similar features can be omitted.

Returning to FIGS. 1A and 1B, upon final assembly of the counter 10, the engagement assembly 80 and the display assembly 82 of the tracking and display unit 22 operate in tandem to generate (or "track") and display information indicative of a distance of travel of the elongated medical device 12 traveling along the passageway 34 as described in greater detail below. In general terms, with the engagement surface 140 (FIG. 3D) engaged with the elongated medical device 12, the engagement assembly 80 rotates with travel of the elongated medical device 12 through or along the passageway 34; the portion of the indicia 180 visible in the window 182 changes with rotation of the engagement assembly 82. Because the indicia 180, and in particular the location and value of each of the numbers 190 (labeled in FIG. 4A), correlates with the circumference of the engagement surface 140, the particular portion of the indicia 180 visible in the window 182 at any point in time during traveling movement of the elongated medical device 12, that visible portion indicates the travel distance of the elongated medical device 12.

Figure 5A:
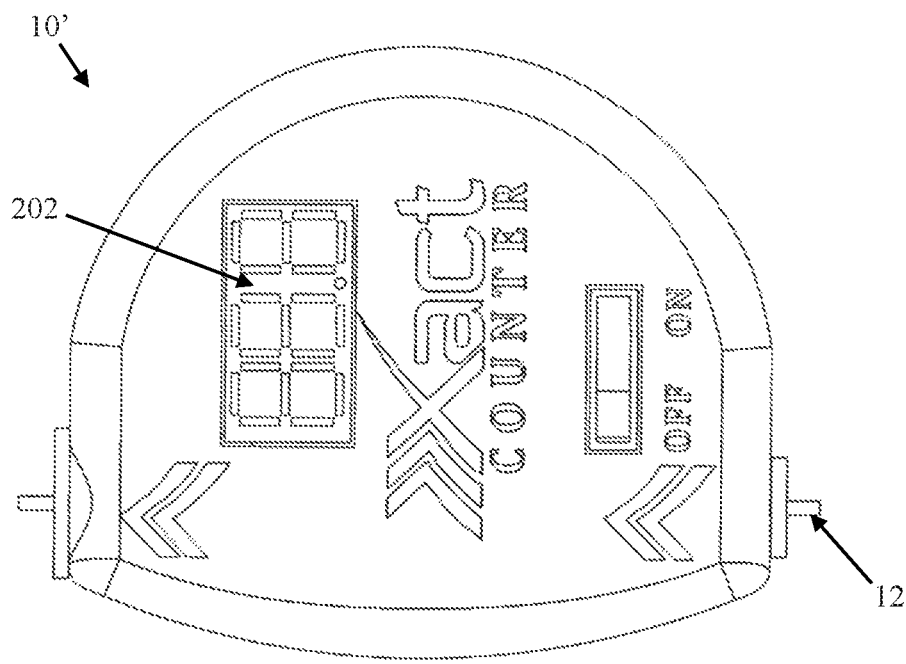
FIG. 5A is a plan view of another counter device in accordance with principles of the present disclosure.
Figure 5B:
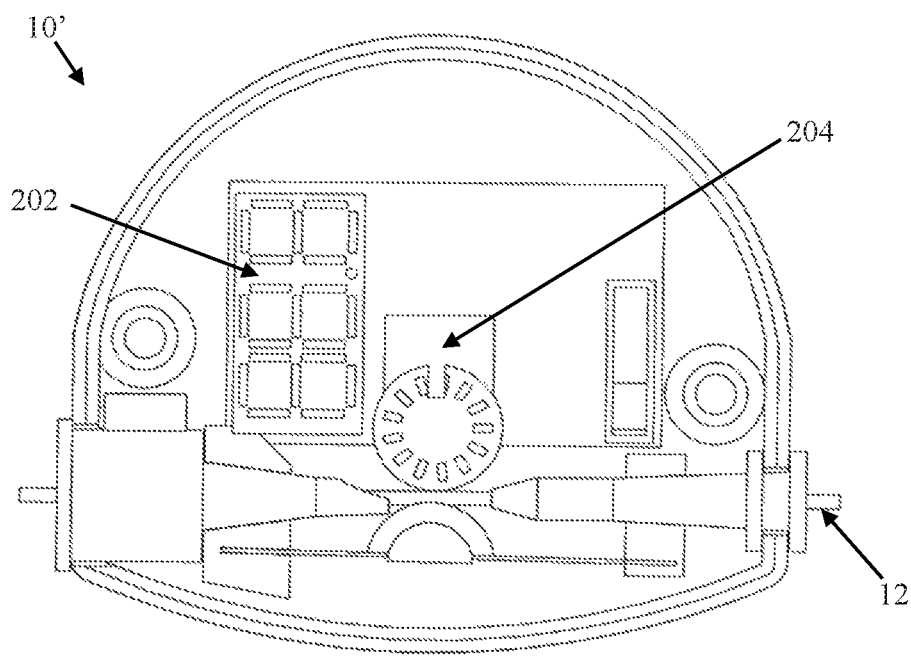
FIG. 5B is a plan view of the counter device of FIG. 5A with a cover portion removed.

While the display assembly 82 has been described as essentially being mechanical in nature, directly tied to mechanical operation of the engagement assembly 80, other configurations are also acceptable. For example, in other embodiments, the display assembly can include or comprise a rotary encoder positioned to monitor revolution of the engagement assembly 80 and a digital display electronically linked to the rotary encoder for displaying distance of travel. FIG. 5A illustrates a non-limiting example of a counter device 10' in accordance with principles of the present disclosure that includes a digital display 202. In the view of FIG. 5B, a front cover of the counter device 10' is removed and reveals a rotary encoder 204 electronically linked to the digital display 202 and that tracks travel of the elongated medical device 12.

Figure 6A:
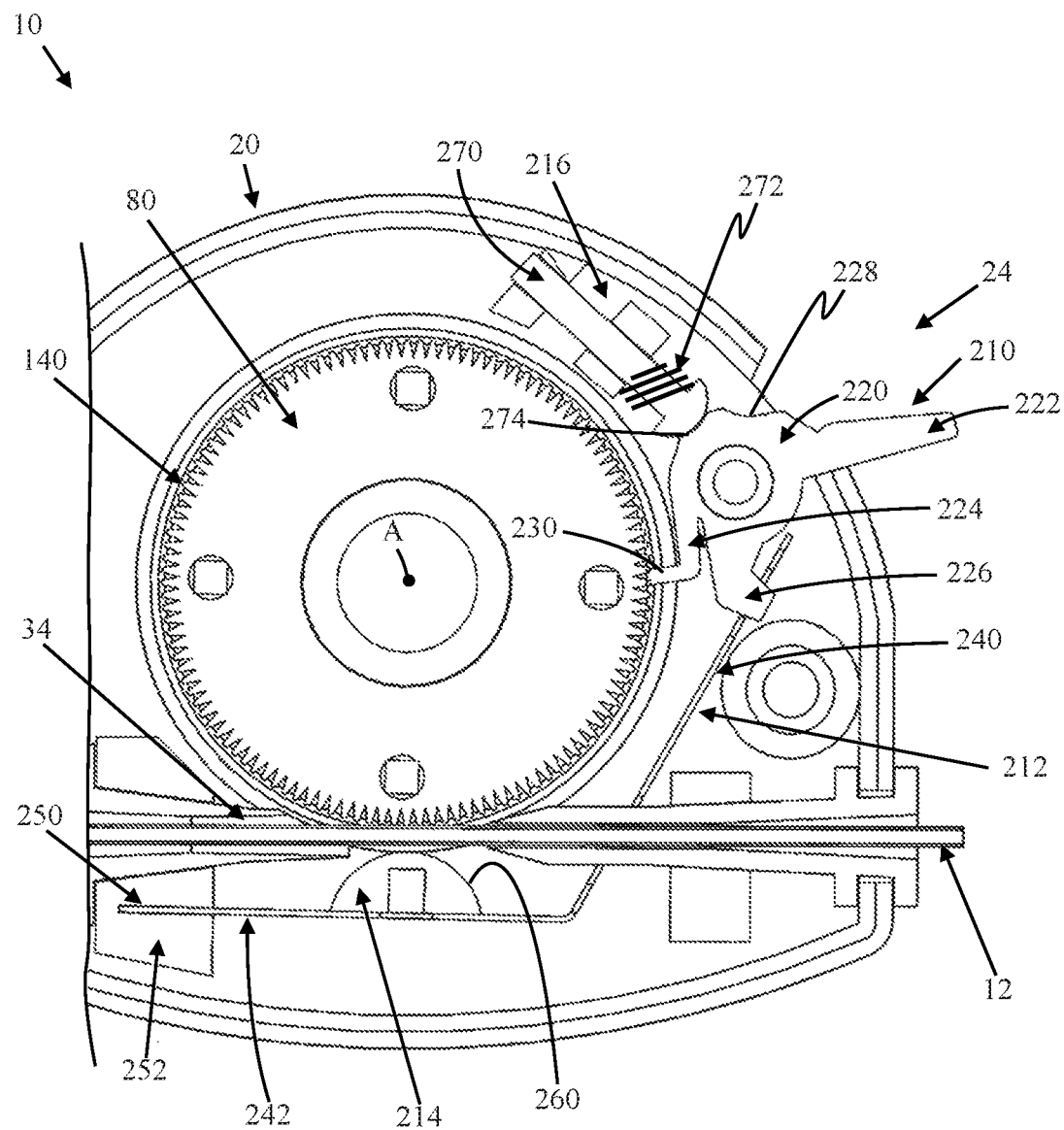
FIG. 6A is an enlarged portion of a lateral cross-sectional view of the counter device of FIG. 1A in an off or no tracking state and carrying an elongated medical device.
Figure 6B:
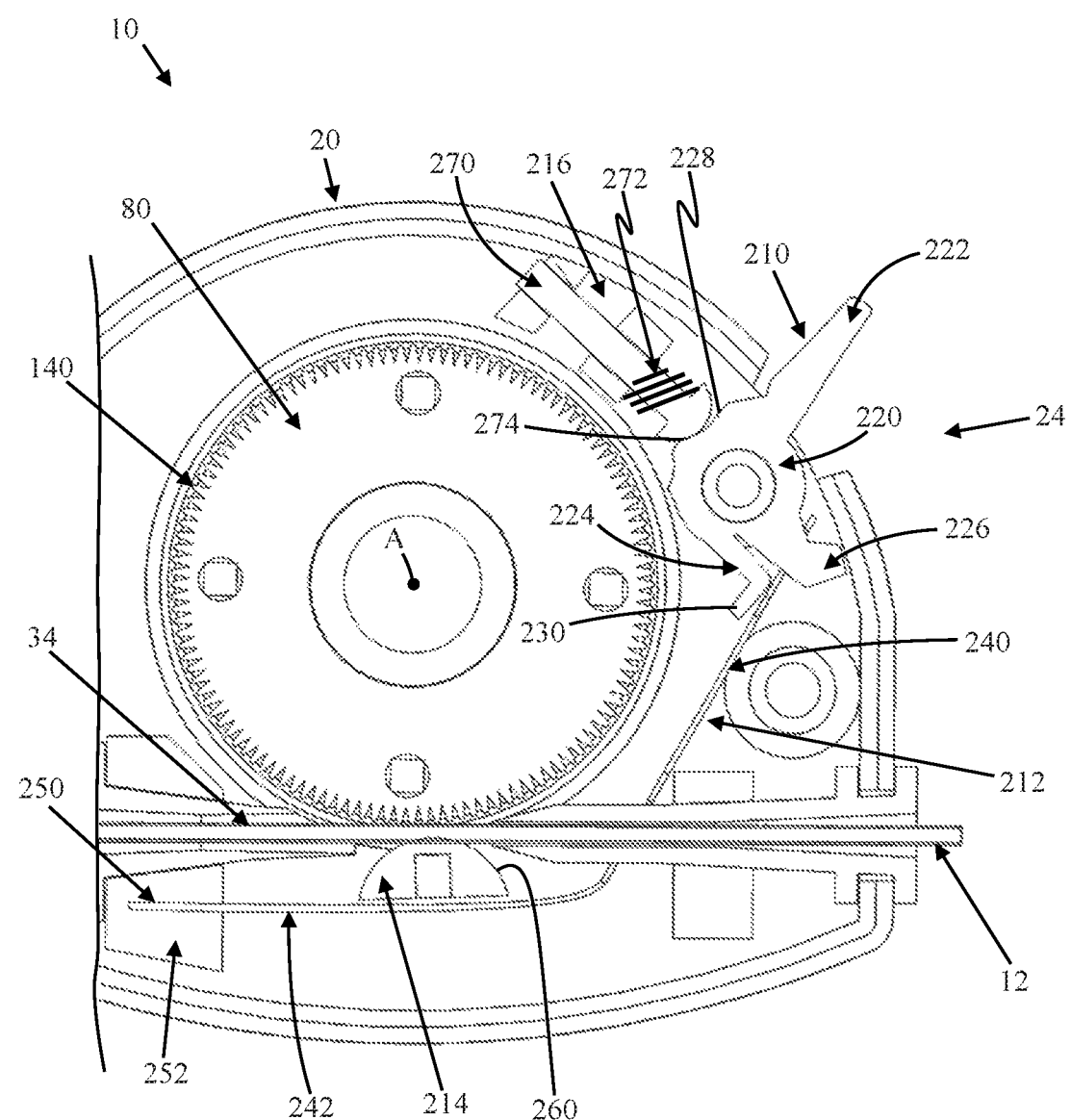
FIG. 6B is a lateral cross-section view of the counter device of FIG. 6B in an on or tracking state.

Actuator Assembly

Where provided, the actuator assembly 24 can assume various forms appropriate to selectively bring the elongated medical device 12 (otherwise disposed along the passageway 34) and the engagement surface 140 (FIG. 3D) into engagement with one another. In some embodiments, and with reference to FIGS. 6A and 6B, the actuator assembly 24 can include a switch body 210, a link 212, a slider block 214, and a lock mechanism 216. As a point of reference, FIG. 6A illustrates the actuator assembly 24 in an "off" or free state, whereas FIG. 6B depicts the "on" or tracking state. Details on the various components are provided below. In general terms, the slider block 214 is maintained by the link 212; articulation of the link 212 by movement of the switch body 210 moves the slider block 214 toward/away from the engagement assembly 80. The slider block 214 is positioned to interface with the elongated medical device 12 (when disposed along the passageway 34). Movement of the slider block 214 toward the engagement assembly 80 brings the elongated medical device 12 into engagement with the engagement surface 140 of the engagement assembly 80 (FIG. 6B); movement of the slider block 214 away from the engagement assembly 80 allows the elongated medical device 12 to release from engagement with (or simply not engage) the engagement surface 140 (FIG. 6A). The lock mechanism 216 assists in maintaining the switch body 210 (and thus the link 212/slider block 214) in a selected position.

The switch body 210 includes, in some embodiments, a hub 220, a lever 222, a locking arm 224, and a linkage arm 226. The hub 220 is configured to facilitate rotatable mounting of the switch body 210 to the housing assembly 20 (e.g., via mounting over a post formed by the second housing section 44). A notch 228 is formed along a perimeter of the hub 220 for reasons made clear below. The lever 222 projects radially outwardly from the hub 220, and is generally configured for interface therewith by a user's finger or thumb. The locking arm 224 projects away from the hub 220 apart from the lever 222, terminating in a catch 230 generally configured to selectively interface with the engagement surface 140 as described below. The linkage arm 226 projects from the hub 220 apart from the lever 222 and the locking arm 224, and is generally configured for connection with the link 212.

Figure 6C:
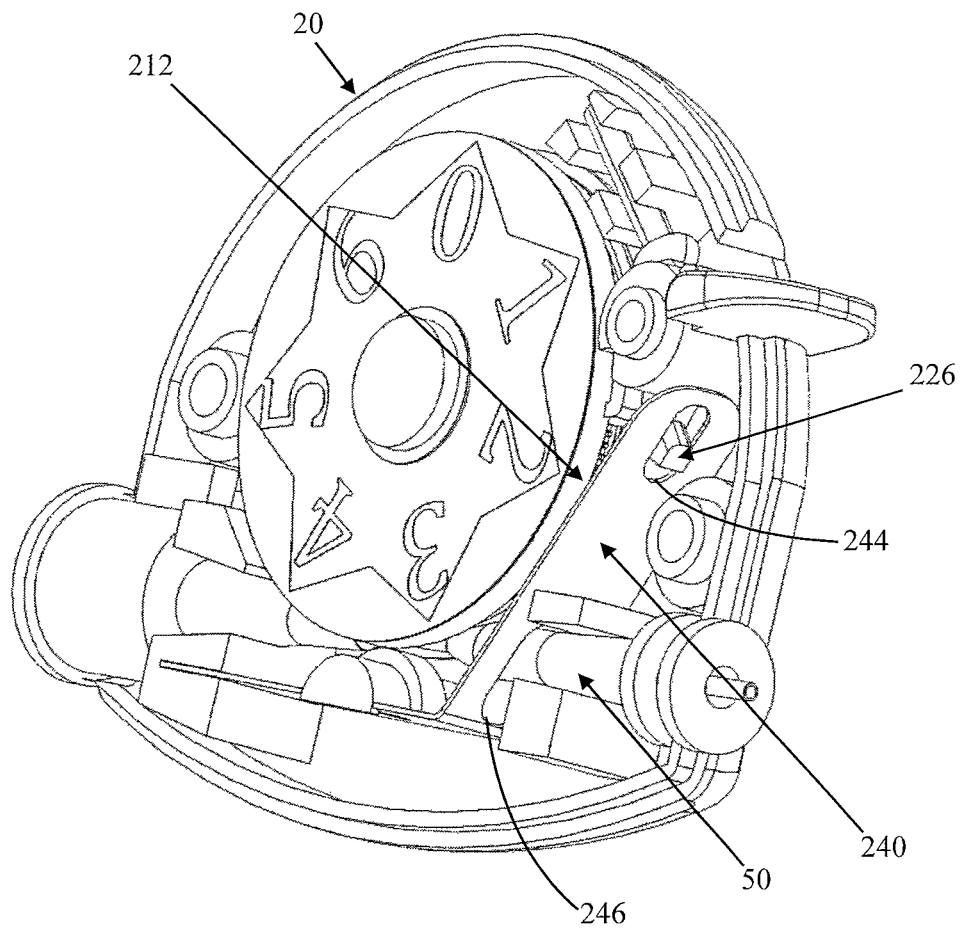
FIG. 6C is a side perspective view of the counter device of FIG. 1A with a portion of a cover assembly removed.

The link 212 can assume various forms, and in some embodiments can be akin to a spring. The link 212 can form or establish a leading segment 240 and a trailing segment 242. The leading segment 240 can include or define features that facilitate connection with the linkage arm 226. For example, as shown in FIG. 6C, the leading segment 240 can form a capture slot 244 sized to slidably receive the linkage arm 226. The leading segment 240 (and/or other portions of the link 212) can include additional features that facilitate mounting to and operation within the housing assembly 20. For example, a clearance slot 246 can be defined along the leading segment 240 that is sized and shaped to receive a portion of the entrance funnel 50. As described below, geometries of the entrance funnel 50 and the clearance slot 246 are such that the link 212 can freely articulate in a desired manner relative to other components, including the entrance funnel 50 (i.e., the entrance funnel 50 does not impede desired movement of the link 212; the link 212 freely slides over the entrance funnel 50 via the clearance slot 246).

Returning to FIGS. 6A and 6B, the trailing segment 242 projects from the leading segment 240, terminating at a pivot end 250. The pivot end 250 is configured for attachment to the housing assembly 20, for example press-fit attachment to a retention block 252. Regardless, an angle of extension or geometry of the trailing segment 242 relative to the leading segment 240 is selected to generate a desired direction of movement of the trailing segment 242 (with the link 212 pivoting at the pivot end 250) as described in greater detail below.

The slider block 214 is configured for low frictional interface with a traveling elongated medical device, such as a catheter (e.g., a conventional epidural catheter). In some embodiments, the slider block 214 forms or defines a curved or arcuate interface surface 260, and is formed of a material selected to have a low coefficient of friction with an elongated medical device expected to be used with the counter device 10. For example, the slider block 214 can be formed of a polymer material or resin, such as Delrin® acetyl homopolymer, acetyl copolymer, etc. Regardless, the slider body 214 is configured for attachment to the trailing segment 242 of the link 212 (e.g., molding, adhesive, etc.). Upon final assembly, the interface surface 260 is projects away from the trailing segment 242 (e.g., the interface surface 260 can form a convex curve relative to the trailing segment 242).

The lock mechanism 216 can assume various forms appropriate for selectively interfacing with the switch body 210, and in some embodiments includes a pin 270 and a biasing member 272. The pin 270 serves as a detent, terminating in a head 274 sized and shaped to nest within the notch 228 of the switch body 210. The pin 270 can be slidably retained by the housing assembly 20 in various fashions, with the biasing member 272 (e.g., a compression spring) biasing the head 274 toward or into contact with the switch body 210.

Upon final assembly, the switch body 210 is rotatably coupled to the housing assembly 20 as described above, with the lever 222 projecting through a slot in the housing 40 so as to be accessible by a user. The switch body 210 is rotatable relative to the housing assembly 20 between a tracking or "on" position and a free or "off" position. As a point of reference, FIG. 6B depicts the switch body 210 in the "on" position as can be visually identified to a user as reflected, for example, by FIG. 1A. Rotation of the switch body 210 from the "on" position to the "off" position (FIG. 6A) articulates the catch 230 of the locking arm 224 toward the engagement assembly 80; rotation of the switch body 210 from the "off" position to the "on" position articulates the catch 230 away from the engagement assembly 80. A geometry and location of the switch body 210 relative to the engagement assembly 80 is such that in the "off" position of the switch body 210, the catch 230 couples to the engagement surface 140 (e.g., nests between two of the teeth 142 (identified in FIG. 3E)). With this construction, when the switch body 210 is held in the "off" position, the switch body 210 serves to prevent the engagement assembly 80 from rotating. The link 212 is retained within the housing assembly 20 as described above. A geometry and location of the switch body 210 relative to the link 212 is such that as the switch body 210 is rotated from the "off" position to the "on" position, the linkage arm 226 is brought into robust contact or engagement with the leading segment 240 (i.e., at an end of the capture slot 244 (FIG. 6C)). With further movement of the switch body 210 toward the "on" position, the linkage arm 226 applies a force onto the link 212, with the link 212 in turn pivoting at the pivot end 250. The link 212 is thus forced or caused to move generally in an upward direction (relative to the orientation of FIGS. 6A and 6B). A geometry of the trailing segment 242 relative to the leading segment 240 is such that in conjunction with this motion, the slider block 214 is directed toward the engagement assembly 80 (e.g., in a direction that is generally radial or transverse to the central axis A). Where the elongated medical device 12 is positioned along the passageway 34 (i.e., between the engagement surface 140 and the slider block 214), movement of the slider block 214 toward the engagement assembly 80 brings the slider block 214 into intimate contact with the elongated medical device 12, applying a spring-type force, with the trailing end 242 acting as a leaf spring, onto the elongated medical device 12 and into contact or engagement with the engagement surface 140. In this regard, the curved or arcuate shape of the interface surface 260 is such that even in this engaged state, the elongated medical device 12 readily slides along the interface surface 260. Thus, the elongated medical device 12 can travel along the passageway 34, sliding along the interface surface 260 but causing the engagement assembly 80 to rotate (due to the engaged relationship between the elongated medical device 12 and the engagement surface 140). The locking mechanism 216 operates to prevent the switch body 210 from unintentionally rotating away from the "on" position via locked interface between the pin 270 and the switch body 210 at the notch 228. Where desired, a user can transition the switch body 210 from the "on" position (or from the "off" position) by applying a force onto the lever 222.

The actuator assembly 24 can have a variety of other formats that may or may not include one or more of the switch body 210, the link 212, the slider block 214 or the locking mechanism 216 as described in above. In more general terms, any construction capable of selectively bringing the elongated medical device 12 (otherwise disposed along the passageway 34) and the engagement surface 140 into contact with one another in response to a user-initiated prompt is acceptable. For example, the actuator assembly 24 can be configured to move the engagement assembly 80 relative to the elongated medical device 12. In a broader sense, the actuator assembly 24 can be viewed or considered as being operable to change a shape of the passageway 34; in one state, a size of the passageway 34 in a region of the engagement assembly 80 is sufficient for the elongated medical device 12 to clear or not robustly contact the engagement surface 140, and in a second state the passageway 34 in a region of the engagement assembly 80 forces the elongated medical device 12 to contact the engagement surface 140. In yet other embodiments, the counter devices of the present disclosure can be configured such that the elongated medical device 12 is always in contact with the engagement assembly 80 during use such that the actuator assembly can be omitted.

Methods of Use

Figure 7A:
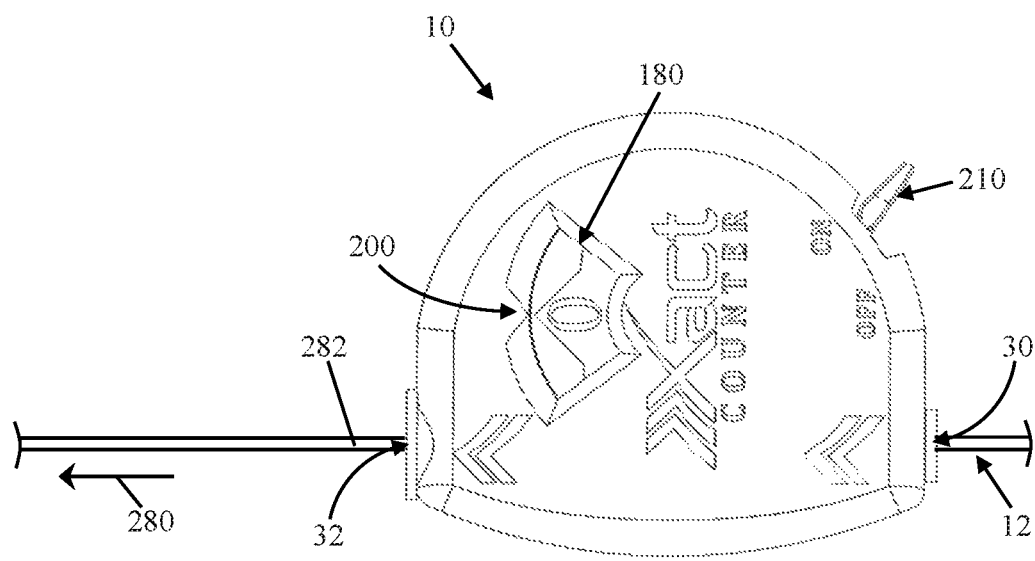
FIGS. 7A-9B illustrate operation of the counter device of FIG. 1A in tracking movement of an elongated medical device.
Figure 7B:
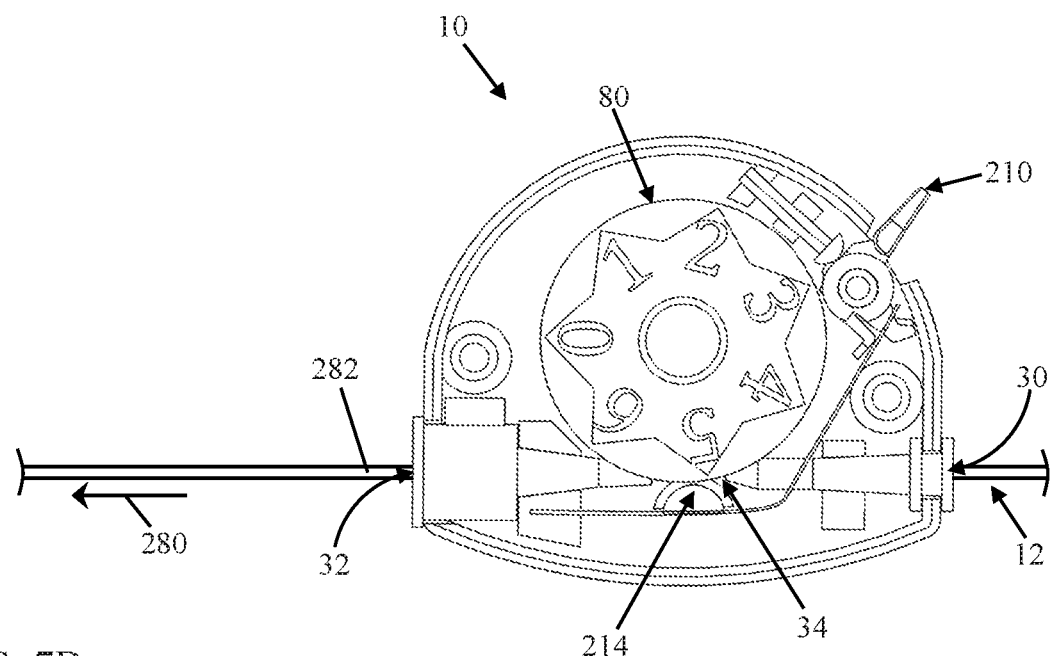

With reference to FIGS. 7A and 7B, use of the counter device 10 in tracking a travel distance of the elongated medical device 12 can including initially loading the counter device 10 over the elongated medical device 12. The elongated medical device 12 is inserted through either of the entrance or exit openings 30, 32, guided through the passageway 34 (referenced generally in FIG. 7B), and extended through the other of the entrance or exit openings 30, 32. When loaded, a length of the elongated medical device 12 extends proximally beyond the entrance opening 30, and a length extends distally beyond the exit opening 32. The counter device 10 is transitioned to the tracking state, such as by articulating the switch body 210 to the "on" position as shown. In the tracking state, the elongated medical device 12 is engaged with the engagement assembly 80 as described above. In this regard, the counter device 10 can be provided to a user such that when first transitioned to the tracking state, a travel distance value of "0" is visually conveyed to the user (e.g., the number "0" is visible in the window 180 and is aligned with the pointer 200). For example, as originally shipped or provided to a user, the counter device 10 can be arranged as shown, except that the switch body 210 is in the "off" position. As described above, in the "off" position, the actuator assembly 80 cannot rotate, thus assuring that when the user does decide to transition the switch body 210 to the on position, the travel distance value of "0" will be displayed. The user can load the counter device 10 onto the elongated medical device 12 as described above with the switch body 210 in the "off" position, and the travel distance value of "0" will not change. Only when the user is ready to track advancement of the elongated medical device 12 and the switch body 210 articulated to the "on" position can the displayed travel distance value change. In other embodiments, the counter device 10 can be configured to allow a user to "re-set" the travel distance display value to "0" manually.

Figure 8A:
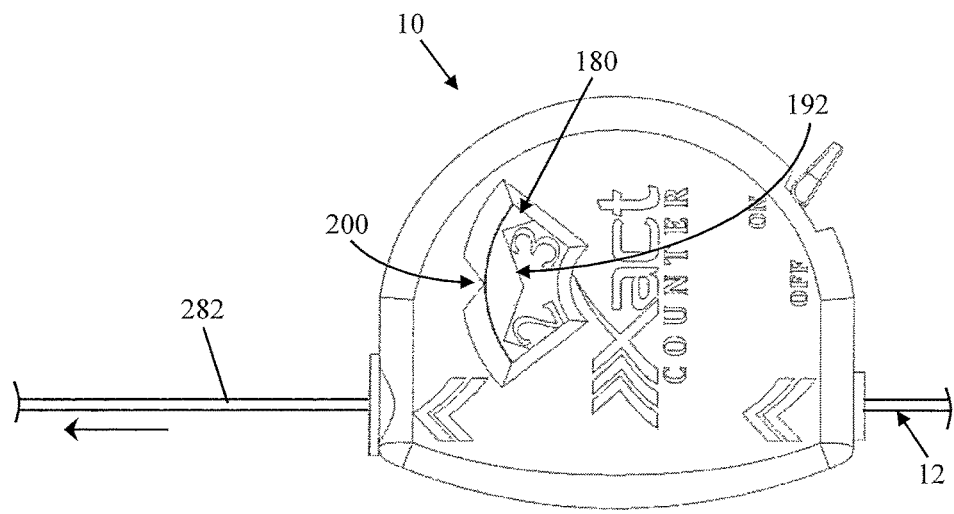
Figure 8B:
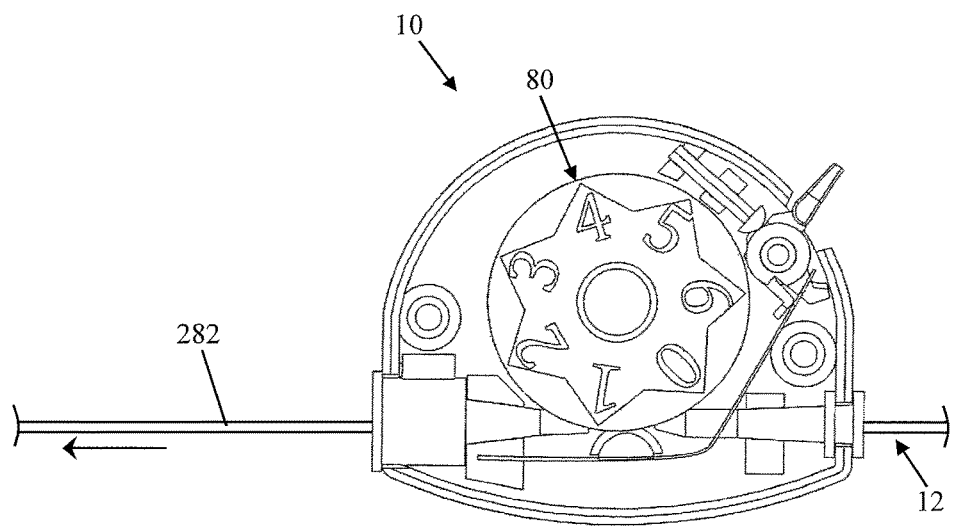

The elongated medical device 12 can then be advanced relative to the counter device 10 as indicated by arrow 280. For ease of explanation, a point 282 along the elongated medical device 12 is identified in FIGS. 7A and 7B. Advancement of the elongated medical device 12 relative to the counter device 10 entails the point 282 moving left-ward relative to an orientation of the views. With advancement, the elongated medical device 12 travels along the passageway 34, sliding along the slider block 214. Due to engagement between the elongated medical device 12 and the engagement surface 140 (FIG. 6A), the engagement assembly 80 is caused to rotate with advancement of the elongated medical device 12. FIGS. 8A and 8B reflect a later stage of advancement of the elongated medical device 12 relative to the counter device 10. A comparison of FIGS. 7A and 7B with FIGS. 8A and 8B reveals that the point 282 has moved or traveled, and that the engagement assembly 80 has been caused to rotate in tracking movement of the elongated medical device 12. At the point in time reflected by FIGS. 8A and 8B, the counter device 10 visually conveys to a user a travel distance value of approximately 2.5 (e.g., the numbers "2" and "3" are visible in the window 180, with the pointer 200 generally aligned mid-way between "2" and "3" as further implicated by the increment indicia 192 as described above). In some examples where the counter device 10 is configured to track and convey travel distances in terms of centimeters, a user readily understands that the elongated medical device 12 has been advanced, or traveled, 2.5 centimeters (from the initial location of FIGS. 7A and 7B). In other words, the point 282 has moved or advanced approximately 2.5 centimeters relative to the counter device 10 from the initial arrangement.

Figure 9A:
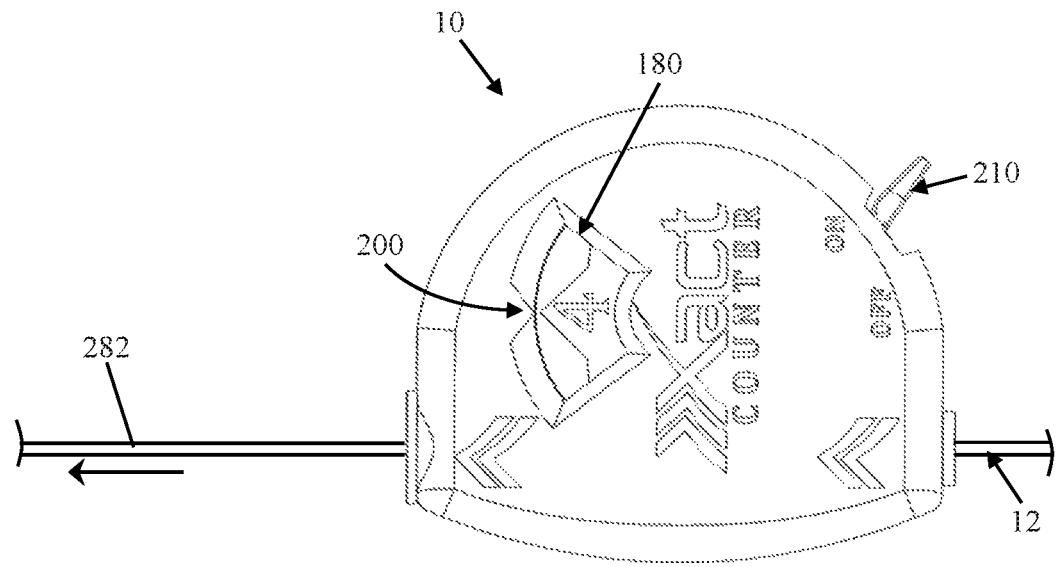
Figure 9B:
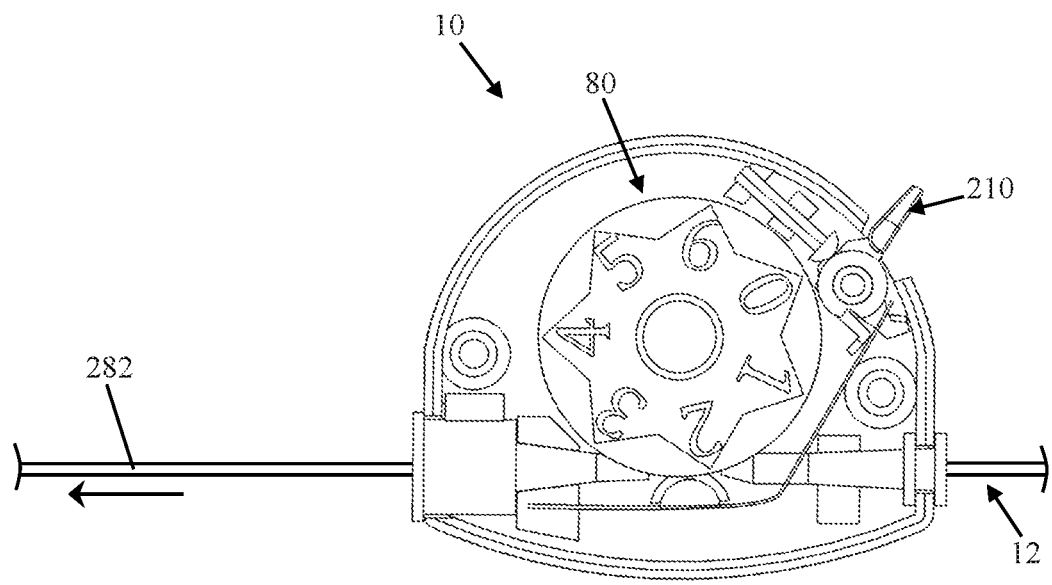

User advancement (or retraction) of the elongated medical device 12 relative to the counter device 10 can continue as desired by the user. FIGS. 9A and 9B reflect another possible later stage of advancement of the elongated medical device 12. A comparison of FIGS. 7A and 7B with FIGS. 9A and 9B reveals that the point 282 has moved or traveled, and that the engagement assembly 80 has been caused to rotate in tracking movement of the elongated medical device 12. At the point in time reflected by FIGS. 9A and 9B, the counter device 10 visually conveys to a travel distance value of approximately 4 (e.g., the number "4" is visible in the window 180, as is generally aligned with the pointer 200). In some examples where the counter device 10 is configured to track and convey travel distances in terms of centimeters, a user readily understands that the elongated medical device 12 has been advanced, or traveled, 4 centimeters (from the initial location of FIGS. 7A and 7B). In other words, the point 282 has moved or advanced approximately 4 centimeters relative to the counter device 10 from the initial arrangement. Notably, if the user retracts the elongated medical device 12 relative to the counter device 10 (e.g., moves the elongated medical device 12 left-ward relative to the orientation of the views), the engagement assembly 80 is caused to rotate in an opposite direction. Thus, for example, the elongated medical device 12 can be retracted relative to the counter device from the arrangement of FIGS. 9A and 9B to the arrangement of FIGS. 8A and 8B; the travel distance information conveyed by the counter device 10 will change accordingly such that the displayed travel distance is always relative to the initial position of the elongated medical device 12 relative to the counter device 10 at the point in time when the switch body 210 is first moved to the on position.

Medical Treatment Kits or Systems

Figure 10:
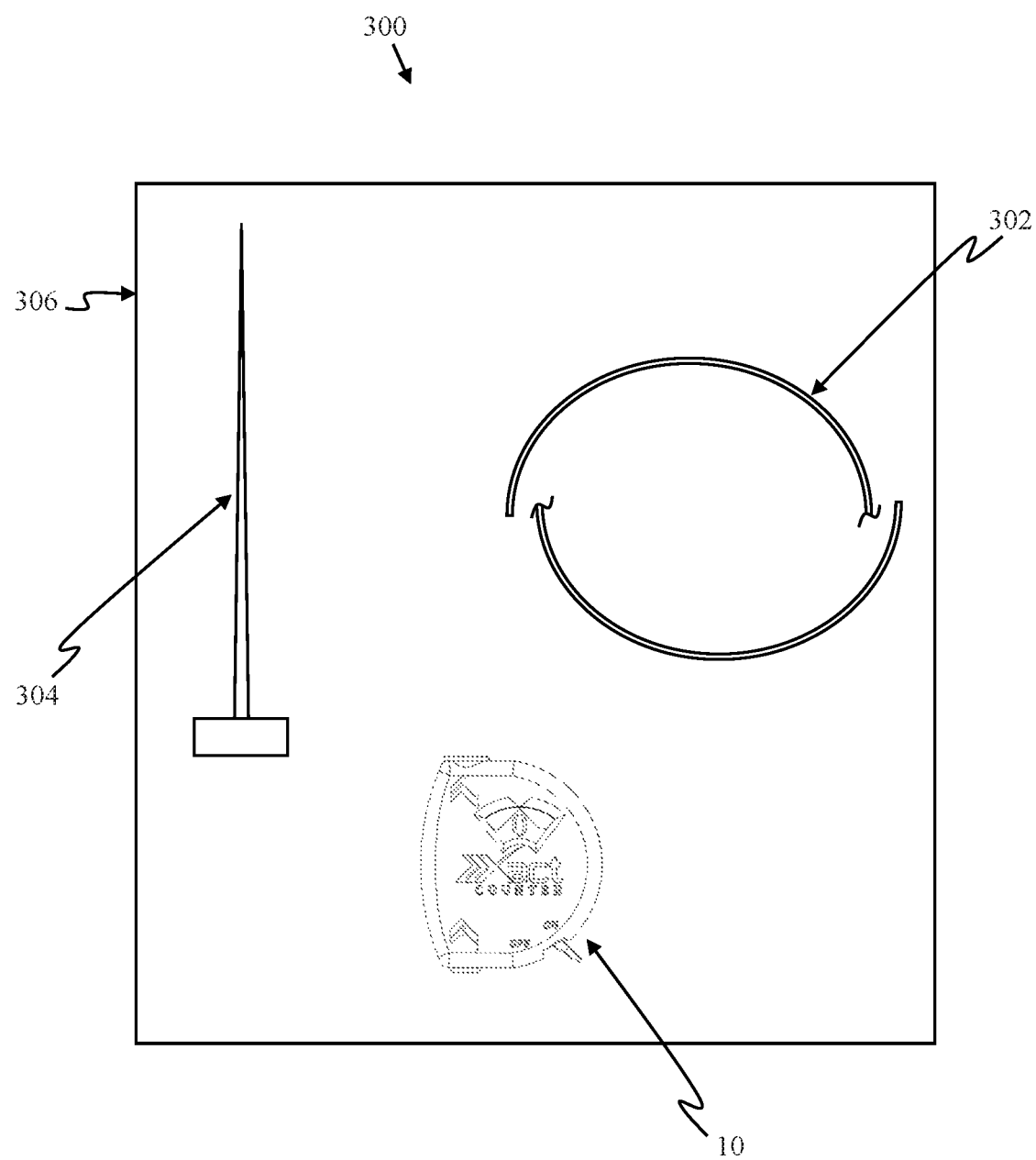
FIG. 10 is a simplified plan view of a kit or system for performing a medical procedure, such as an epidural anesthesia administration procedure.

As mentioned above, the counter devices of the present disclosure can be useful with a variety of different elongated medical devices. In some embodiments, the counter device is provided as part of a system for performing a medical procedure, where the system includes both the counter device and the elongated medical device. FIG. 10 illustrates one embodiment of a system or kit 300 for performing a medical procedure, for example an epidural anesthesia administration procedure. The system 300 includes the counter device 10 as described above, an elongated medical device such as an epidural catheter 302, an optional spinal needle 304, and optional packaging 306. The epidural catheter 302 can assume any type known the art appropriate for epidural anesthesia administration. Where provided, the spinal needle 304 can also have any form known in the art useful with epidural anesthesia administration procedures and can be or include, for example, a Tuohy needle. The packaging 306, where provided, encases and is sealed about at least the counter device 10 and the epidural catheter 302, for example maintaining a sterility of the counter device 10 and the epidural catheter 302 (i.e., the counter device 10 and the epidural catheter 302 are sterilized prior to insertion into the packaging 306).

The kit or system 300 can be provided to a user as described above. An epidural anesthesia administration procedure can then be performed on a patient in a surgically safe environment by first removing the counter device 10 and the epidural catheter 302 from the packaging 306. The epidural anesthesia administration procedure can then be performed in accordance with methods of the present disclosure. In some embodiments, a needle device (e.g., the spinal needle 304) is manipulated by a clinician to locate a needle tip at the epidural space. The epidural catheter 302 is then advanced through the needle and into the patient until a length of the catheter extends to the needle tip and slightly into the epidural space. The clinician may tactilely sense or feel that the epidural catheter 302 as progressed just beyond the needle tip by a change in resistance to advancement as the epidural catheter 302 exits the needle tip. The counter device 10 (in the off position or free state) is then loaded onto the epidural catheter 302 as described above at location proximal the needle device. Once the counter device 10 is at a desired location along a length of the epidural catheter 302, the counter device 10 is transitioned to the engaged state or on position. The clinician then advances (and/or retracts) the epidural catheter 302 relative to the counter device 10 and the needle device as desired, with the counter device 10 tracking and displaying information indicating a travel distance of the epidural catheter 302. The counter device 10 thus provides the clinician with assurances that the epidural catheter 302 has advanced into the epidural space (i.e., distally progressed beyond the needle tip) a desired distance and/or has not been advance beyond a maximum distance. Once satisfied with placement of the epidural catheter 302, the counter device 10 and the spinal needle 304 are withdrawn over the epidural catheter 302. Anesthetics or other liquids are then injected into the epidural space via the epidural catheter 302.

The counter devices, treatment systems or kits, and methods of the present disclosure provide a marked improvement over previous designs. The counter devices track movement or advancement of an elongated medical device, and provide a user with information indicative of the travel distance of the elongated medical device. When used, for example, with an epidural catheter as part of an epidural anesthesia administration procedure, a clinician can more confidently locate the epidural catheter at a desired location.

Although the present disclosure has been described with reference to preferred embodiments, workers skilled in the art will recognize that changes can be made in form and detail without departing from the spirit and scope of the present disclosure.

What is claimed is:

1. A counter device for use with an elongated medical device, the counter device comprising:
    a housing assembly defining an entrance opening, an exit opening and a passageway open to and extending between the entrance and exit openings;
    a tracking and display unit carried by the housing assembly and configured to selectively interface with an elongated medical device disposed along the passageway, the tracking and display unit including an engagement assembly rotatably coupled to the housing assembly and configured to selectively engage the elongated medical device traveling along the passageway;
    wherein the engagement assembly is ring-shaped, and the housing assembly comprises an outer housing and a pin projecting from a wall of the outer housing, and further wherein the engagement assembly is rotatable about the pin;
    wherein the tracking and display unit further comprises:
        indicia disposed on the engagement assembly, the indicia representative of units of distance; and
        a window formed in the outer housing;
        wherein the engagement assembly is maintained relative to the outer housing such that the indicia is selectively visible in the window; and
    an actuator assembly including a slider block, the actuator assembly configured to selectively alter a distance between the slider block and the engagement assembly;
    wherein the counter device is configured to provide:
        a tracking state in which the tracking and display unit generates information indicative of a distance of travel of the elongated medical device traveling along the passageway.

2. The counter device of claim 1, wherein the indicia includes a plurality of numbers, and further wherein a circumferential distance between immediately adjacent ones of the plurality of numbers corresponds with a distance of travel of 1 centimeter.

3. The counter device of claim 1, wherein the tracking and display unit further comprises a rotary encoder positioned to monitor revolution of the engagement assembly and a B digital display electronically linked to the rotary encoder for displaying a distance of travel.

4. The counter device of claim 1, wherein the engagement assembly comprises:
    opposing, first and second outer hub bodies; and
    a ring disposed between the outer hub bodies;
    wherein a diameter of the ring is greater than a diameter of each of the first and second outer hub bodies at a location immediately adjacent the ring.

5. The counter device of claim 4, wherein the ring defines a toothed engagement face for engaging the elongated medical device.

6. The counter device of claim 1, wherein the actuator assembly is operable to define the tracking state and a free state in which the tracking and display unit does not actively track the elongated medical device traveling along the passageway, and further wherein a distance between the slider block and the engagement assembly in the tracking state is less than a distance between the slider block and the engagement assembly in the free state.

7. A kit for performing a medical procedure, the kit comprising:
    an elongated medical device; and
    a counter device comprising:
        a housing assembly defining an entrance opening, an exit opening and a passageway open to and extending between the entrance and exit openings, a tracking and display unit carried by the housing assembly and configured to selectively interface with the elongated medical device when disposed along the passageway, wherein the tracking and display unit includes an engagement assembly rotatably coupled to the housing assembly, the engagement assembly comprising:
opposing, first and second outer hub bodies, and
a ring disposed between the outer hub bodies,
wherein a diameter of the ring is greater than a diameter of each of the first and second outer hub bodies at a location immediately adjacent the ring;

wherein the counter device is configured to slidably receive the elongated medical device along the passageway and to provide:
a tracking state in which the tracking and display unit generates information indicative of a distance of travel of the elongated medical device traveling along the passageway.

8. The kit of claim 7, wherein the elongated medical device is selected from the group consisting of a catheter and a guidewire.

9. The kit of claim 8, further comprising:
a spinal needle.

10. The kit of claim 7, further comprising:
packaging sealed about the elongated medical device and the counter device.

11. The kit of claim 7, wherein the engagement assembly is configured to selectively engage the elongated medical device when traveling along the passageway.

12. The kit of claim 11, wherein the engagement assembly is ring-shaped, and the housing assembly comprises an outer housing and a pin projecting from a wall of the outer housing, and further wherein the engagement assembly is rotatable about the pin.

13. The kit of claim 12, wherein the tracking and display unit further comprises:
indicia disposed on the engagement assembly, the indicia representative of units of distance; and
a window formed in the outer housing;
wherein the engagement assembly is maintained relative to the outer housing such that the indicia is selectively visible in the window.

14. A counter device for use with an elongated medical device, the counter device comprising:
a housing assembly defining an entrance opening, an exit opening and a passageway open to and extending between the entrance and exit openings; and
a tracking and display unit carried by the housing assembly and configured to selectively interface with an elongated medical device disposed along the passageway;

wherein the tracking and display unit includes an engagement assembly rotatably coupled to the housing assembly comprising:
opposing, first and second outer hub bodies, and
a ring disposed between the outer hub bodies,
wherein a diameter of the ring is greater than a diameter of each of the first and second outer hub bodies at a location immediately adjacent the ring,
wherein the counter device is configured to provide:
a tracking state in which the tracking and display unit generates information indicative of a distance of travel of the elongated medical device traveling along the passageway.

15. The counter device of claim 14, wherein the engagement assembly is ring-shaped, and the housing assembly comprises an outer housing and a pin projecting from a wall of the outer housing, and further wherein the engagement assembly is rotatable about the pin.

16. The counter device of claim 15, wherein the tracking and display unit further comprises:
indicia disposed on the engagement assembly, the indicia representative of units of distance; and
a window formed in the outer housing;
wherein the engagement assembly is maintained relative to the outer housing such that the indicia is selectively visible in the window.

17. The counter device of claim 16, wherein the indicia includes a plurality of numbers, and further wherein a circumferential distance between immediately adjacent ones of the plurality of numbers corresponds with a distance of travel of 1 centimeter.

18. The counter device of claim 14, wherein the tracking and display unit further comprises a rotary encoder positioned to monitor revolution of the engagement assembly and a digital display electronically linked to the rotary encoder for displaying distance of travel.

19. The counter device of claim 14, wherein the ring defines a toothed engagement face for engaging the elongated medical device.

* * * * *